United States Patent
Okaki

(10) Patent No.: US 12,370,140 B2
(45) Date of Patent: Jul. 29, 2025

(54) MICELLE FOR SOLUBILIZING A SPARINGLY WATER-SOLUBLE INGREDIENT AND SOLUTION COMPRISING THE SAME

(71) Applicant: TEIKA PHARMACEUTICAL CO., LTD., Toyama (JP)

(72) Inventor: Toru Okaki, Toyama (JP)

(73) Assignee: TEIKA PHARMACEUTICAL CO., LTD., Toyama (JP)

( * ) Notice: Subject to any disclaimer, the term of this patent is extended or adjusted under 35 U.S.C. 154(b) by 419 days.

(21) Appl. No.: 17/711,280

(22) Filed: Apr. 1, 2022

(65) Prior Publication Data

US 2022/0233438 A1 Jul. 28, 2022

Related U.S. Application Data

(62) Division of application No. 16/618,435, filed as application No. PCT/JP2018/021129 on Jun. 1, 2018, now Pat. No. 11,318,095.

(30) Foreign Application Priority Data

Jun. 2, 2017 (JP) ................. 2017-110489

(51) Int. Cl.
*A61K 9/107* (2006.01)
*A61K 45/06* (2006.01)
*A61K 47/32* (2006.01)

(52) U.S. Cl.
CPC .............. *A61K 9/107* (2013.01); *A61K 45/06* (2013.01); *A61K 47/32* (2013.01)

(58) Field of Classification Search
None
See application file for complete search history.

(56) References Cited

U.S. PATENT DOCUMENTS

| | | |
|---|---|---|
| 2001/0021390 A1 | 9/2001 | Lau |
| 2006/0140991 A1 | 6/2006 | Makino |
| 2009/0170944 A1 | 7/2009 | Lambert |
| 2011/0021443 A1 | 1/2011 | Lambert et al. |
| 2012/0219600 A1 | 8/2012 | Perumal et al. |

FOREIGN PATENT DOCUMENTS

| | | | | |
|---|---|---|---|---|
| CN | 102066399 | 5/2011 | | |
| EP | 0 639 376 | 2/1995 | | |
| JP | 7-109218 | 4/1995 | | |
| JP | 2003-519083 | 6/2003 | | |
| JP | 2004-161739 | 6/2004 | | |
| JP | 2009-510082 | 3/2009 | | |
| JP | 2011-241147 | 12/2011 | | |
| JP | 2011241147 A | * 12/2011 | ........... A61K 31/405 |
| JP | 5308824 | 7/2013 | | |
| WO | 00/21510 | 4/2000 | | |
| WO | 2005/018607 | 3/2005 | | |
| WO | 2007/038627 | 4/2007 | | |
| WO | 2007/070517 | 6/2007 | | |
| WO | 2009/137112 | 11/2009 | | |
| WO | 2009/140429 | 11/2009 | | |
| WO | 2010/023908 | 3/2010 | | |

OTHER PUBLICATIONS

Indomethacin (Cayman Product Information Sheet, accessed online Jul. 18, 2024). (Year: 2024).*
Swettis Beauty Blog (How to adjust the pH of your cosmetic products, May 25, 2017). (Year: 2017).*
International Search Report (ISR) issued Aug. 14, 2018 in International (PCT) Application No. PCT/JP2018/021129.
Allegra (R) Tablet Interview Form, Dec. 2015, cited in the specification, with partial English translation.
Sabrina Consola et al., "Design of Original Bioactive Formulations Based on Sugar-Surfactant/Non-steroidal Anti-inflammatory Catanionic Self-Assemblies: A New Way of Dermal Drug Delivery", Chem. Eur. J., vol. 13, No. 11, pp. 3039-3047, in particular, see abstract, results and discussion, scheme 1, fig. 4-6, 2007.
International Preliminary Report on Patentability issued Dec. 12, 2019 in International (PCT) Application No. PCT/JP2018/021129.
Extended European Search Report issued Feb. 16, 2021 in corresponding European Patent Application No. 18809663.0.

* cited by examiner

*Primary Examiner* — Melissa S Mercier
(74) *Attorney, Agent, or Firm* — Wenderoth, Lind & Ponack, L.L.P.

(57) ABSTRACT

The present invention provides a micelle comprising an anionic micelle and a protecting agent surrounding the anionic micelle, the anionic micelle being formed from, as a structural unit, an ingredient that has a functional group capable of being anionized under basic conditions and has anionic micelle-forming ability, the protecting agent protecting the anionic micelle. The present invention also provides a micelle comprising a cationic micelle and a protecting agent surrounding the cationic micelle, the cationic micelle being formed from, as a structural unit, an ingredient that has a functional group capable of being cationized under acidic conditions and has cationic micelle-forming ability, the protecting agent protecting the cationic micelle.

13 Claims, 7 Drawing Sheets

Two-dimensional schematic illustration of micelle α or β

Two-dimensional schematic illustration of micelle α2 or β2

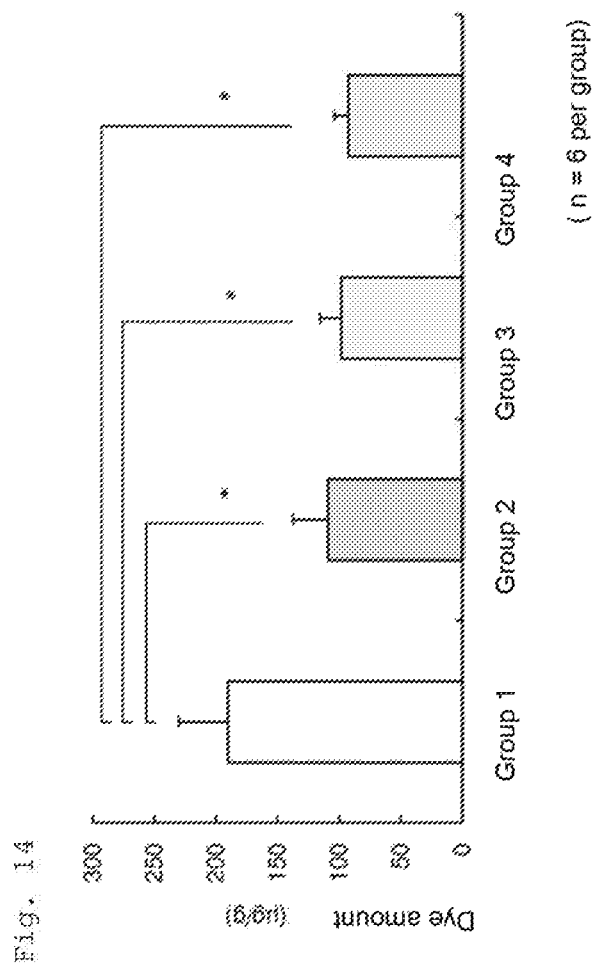

MICELLE FOR SOLUBILIZING A SPARINGLY WATER-SOLUBLE INGREDIENT AND SOLUTION COMPRISING THE SAME

TECHNICAL FIELD

The present invention relates to a micelle for solubilizing a sparingly water-soluble ingredient and a solution comprising the same.

BACKGROUND ART

Fexofenadine is a histamine $H_1$ receptor antagonist used for the treatment of pruritus associated with allergic rhinitis (pollen allergy etc.), urticaria, and skin disease. Fexofenadine is sparingly water-soluble (0.011) (w/v) or less at pH 7; Non Patent Literature 1) and thus is net available in the form of a solution (particularly, an eye drop, a nasal drop, etc.). Known formulations of fexofenadine include a suspension (Patent Literature 1). However, suspensions require a cumbersome preparation procedure before use. For example, users need to shake a container well to disperse an active ingredient uniformly. Formulating solutions containing sparingly water-soluble ingredients such as fexofenadine will require immense facility investment and high production cost, which are a hurdle to overcome. Suspensions also have a problem in that they cannot be sterilized by membrane filtration, and therefore, it seems difficult to assure the sterility and quality of suspensions.

Meanwhile, as a solubilization technology for fexofenadine, cyclodextrin inclusion complexation is known (Patent Literature 2). However, in the verification experiment conducted by the present inventor and others, a fexofenadine-containing formulation produced by the production method described in Example 5 in Patent Literature 2 showed massive precipitation of fexofenadine at room temperature or at pH 6 to 7. This result implies that the technology of Patent Literature 2 has a fatal drawback in terms of pharmaceutical use of fexofenadine-containing solutions. In addition, in the fexofenadine-containing solution produced by the technology of Patent Literature 2, micelles in which an anionic micelle formed from fexofenadine as a structural unit is protected by a protecting agent are not present. The same is true of sparingly water-soluble ingredients other than fexofenadine.

Under such circumstances, there is a need for solutions which contain a sparingly water-soluble ingredient and have sufficient stability for practical use. The stability in this context includes that the water solubility of the sparingly water-soluble ingredient is excellent, at pH 5 to 9, which is a pH range acceptable for mucosal application in humans (the sparingly water-soluble ingredient is unlikely to precipitate); the solution is stable at room temperature for a long period of time; and/or the formulation stability of the solution is excellent.

CITATION LIST

Patent Literature

Patent Literature 1: Japanese Patent No. 5308824
Patent Literature 2: JP-W 2003-519083

Non Patent Literature

Non Patent Literature 1:
Drug interview form of Allegra (registered trademark) tablet

SUMMARY OF INVENTION

Technical Problem

Among the objects of the present invention are the following: to solubilize a sparingly water-soluble ingredient in a solution; to provide a solution containing a sparingly water-soluble ingredient; to increase the solubility of a sparingly water-soluble ingredient in water (e.g., neutral, weakly acidic, weakly basic); and/or to solve the above problems concerning stability.

Solution to Problem

The present inventor and others conducted extensive research to solve the above-described problems. As a result, they found that a sparingly water-soluble ingredient can be solubilized by producing a micelle in which an anionic or cationic micelle formed from the sparingly water-soluble ingredient as a structural unit is protected by a protecting agent, and also found that such micelle formation can solve the above problems. Based on this finding, the present inventor and others conducted further research and completed the present invention.

That is, the present invention relates to the following.

[1] A micelle comprising an anionic micelle and a protecting agent surrounding the anionic micelle, the anionic micelle being formed from, as a structural unit, an ingredient that has a functional group capable of being anionized under basic conditions and has anionic micelle-forming ability, the protecting agent protecting the anionic micelle.

[2] The micelle according to the above [1], wherein the protecting agent has an atom bound to an anionized functional group of the anionic micelle, and the electron density of said atom is smaller than the electron density of the anionized functional group of the anionic micelle.

[3] The micelle according to the above [1] or [2], wherein said atom in the protecting agent is bound to the anionized functional group of the anionic micelle via a hydrogen bond.

[4] The micelle according to any of the above [1] to [3], wherein the protecting agent has a hydroxy group (—OH) in water.

[5] The micelle according to any of the above [1] to [4], wherein the protecting agent is one or more selected from the group consisting of polyethylene glycol, glycerin, propylene glycol, sorbitol, mannitol, N-acetylglucosamine, chondroitin sulfate, glycyrrhizinic acid, hydroxypropylmethyl cellulose, methylcellulose, carboxymethyl cellulose, povidone, polyoxyethylene hydrogenated castor oil, and polysorbate 80.

[6] The micelle according to any of the above [1] to [5], wherein the ingredient has a low water solubility in a neutral pH range of 6 to 8.

[7] The micelle according to any of the above [1] to [6], wherein the ingredient is one or more selected from the group consisting of fexofenadine, rebamipide, indomethacin, L-carbocysteine, ibuprofen, and ursodeoxycholic acid, and salts thereof.

[8] A solution comprising the micelle according to any of the above [1] to [7], the solution comprising a solubilized ingredient having a functional group capable of being anionized under basic conditions.

[9] The solution according to the above [8], wherein the ingredient is present at a concentration of 0.01 to 5.0% (w/v).

[10] The solution according to the above [8] or [9], wherein the solution has a pH of 5 to 9 during long-term storage.

[11] The solution according to any of the above [8] to [10], wherein the solution is an eye drop or a nasal drop.

[12] A production method of a micelle, the micelle comprising an anionic micelle and a protecting agent, the anionic micelle being formed from, as a structural unit, an ingredient that has a functional group capable of being anionized under basic conditions and has anionic micelle-forming ability, the protecting agent protecting the anionic micelle, the production method comprising the following steps (A) and (B):
  (A) suspending, in water, the ingredient that has a functional group capable of being anionized under basic conditions and has anionic micelle-forming ability, and subsequently basifying the resulting suspension; and
  (B) adding the protecting agent.

[13] A micelle produced by the production method according to the above [12], the micelle comprising an anionic micelle and a protecting agent, the anionic micelle being formed from, as a structural unit, an ingredient that has a functional group capable of being anionized under basic conditions and has anionic micelle-forming ability, the protecting agent protecting the anionic micelle.

[14] A method for increasing the solubility of an ingredient that has a functional group capable of being anionized under basic conditions and has anionic micelle-forming ability, the method comprising a step of forming an anionic micelle from the ingredient that has a functional group capable of being anionized under basic conditions and has anionic micelle-forming ability.

[15] A micelle comprising a cationic micelle and a protecting agent surrounding the cationic micelle, the cationic micelle being formed from, as a structural unit, an ingredient that, has a functional group capable of being cationized under acidic conditions and has cationic micelle-forming ability, the protecting agent protecting the cationic micelle.

[16] The micelle according to the above [15], wherein the protecting agent has an atom bound to a cationized functional group of the cationic micelle, and the electron density of said atom is greater than the electron density of the cationized functional group of the cationic micelle.

[17] The micelle according to the above [15] to [16], wherein said atom in the protecting agent is bound to the cationized functional group of the cationic micelle via a cation-π interaction.

[18] The micelle according to any of the above [15] to [17], wherein the protecting agent has a π electron.

[19] The micelle according to any of the above [15] to [18], wherein the protecting agent is tyloxapol.

[20] The micelle according to any of the above [15] to [19], further comprising a surfactant-containing layer in contact with the outer surface of a layer containing the protecting agent.

[21] The micelle according to any of the above [15] to [20], wherein the ingredient is one or more selected from the group consisting of brinzolamide, trimebutine, ethyl aminobenzoate, baclofen, metoclopramide, and lidocaine, and salts thereof.

[22] A solution comprising the micelle according to any of the above [15] to [21], the solution comprising a solubilized ingredient having a functional group capable of being cationized under acidic conditions.

[23] The solution according to the above [22], wherein the ingredient is present at a concentration of 0.01 to 5.0% (w/v).

[24] The solution according to the above [22] or [23], wherein the solution has a pH of 5 to 9 during long-term storage.

[25] The solution according to any of the above [22] to [24], wherein the solution is an eye drop or a nasal drop.

[26] A production method of a micelle, the micelle comprising a cationic micelle and a protecting agent, the cationic micelle being formed from, as a structural unit, an ingredient having a functional group capable of being cationized under acidic conditions, the protecting agent protecting the cationic micelle, the production method comprising the following steps (a) and (b):
  (a) suspending, in water, the ingredient having a functional group capable of being cationized under acidic conditions, and subsequently acidifying the resulting suspension; and
  (b) adding the protecting agent.

[27] A micelle produced by the production method according to the above [26], the micelle comprising a cationic micelle and a protecting agent, the cationic micelle being formed from, as a structural unit, an ingredient having a functional group capable of being cationized under acidic conditions, the protecting agent protecting the cationic micelle.

[28] A method for increasing the solubility of an ingredient having a functional group capable of being cationized under acidic conditions, the method comprising a step of forming a cationic micelle from the ingredient having a functional group capable of being cationized under acidic conditions.

Advantageous Effects Of Invention

The present invention achieves the objects including the following: to solubilize a sparingly water-soluble ingredient in a solution; to provide a solution containing a sparingly water-soluble ingredient; to increase the solubility of a sparingly water-soluble ingredient in water (e.g., neutral, weakly acidic, weakly basic); and/or to solve the above problems concerning stability. According to the present invention, a sparingly water-soluble bioactive ingredient or a sparingly water-soluble active pharmaceutical ingredient can be solubilized without sacrificing its bioactivity or pharmaceutical activity. Therefore, the present invention is advantageous. As used herein, the term "stable" means that a solubilized ingredient, is maintained in a soluble state and prevented from changing into an insoluble state, not meaning that an ingredient is prevented from chemically degrading or coupling with another substance and changing into a different substance.

BRIEF DESCRIPTION OF DRAWINGS

FIG. 14 shows the results of a drug efficacy test of fexofenadine.

DESCRIPTION OF EMBODIMENTS

As used herein, the term "room temperature" refers to the room temperature defined in the Japanese Pharmacopoeia, 17th edition unless otherwise specified. Specifically, the room temperature ranges 1 to 30° C. The term "uncontrolled room temperature" is a concept different, from "room temperature" and refers to a condition where the temperature and humidity are uncontrolled in an ordinary room.

Micelle

The present invention provides a micelle comprising a negatively- or positively-charged micelle and a protecting agent, the negatively- or positively-charged micelle being formed from, as a structural unit, an ingredient having a functional group capable of being negatively or positively charged in a pH range excluding pH 7, the protecting agent protecting the negatively- or positively-charged micelle. Specifically, the present invention provides (a) a micelle comprising an anionic micelle and a protecting agent, the anionic micelle being formed from, as a structural unit, an ingredient that has a functional group capable of being anionized under basic conditions and has anionic micelle-forming ability, the protecting agent protecting the anionic micelle (hereinafter also called a micelle α); and/or (β) a micelle comprising a cationic micelle and a protecting agent, the cationic micelle being formed from, as a structural unit, an ingredient having a functional group capable of being cationized under acidic conditions, the protecting agent protecting the cationic micelle (hereinafter also called a micelle β).

Figure 1:
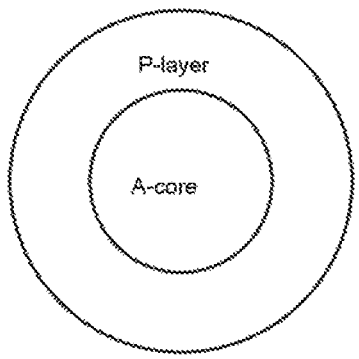
FIG. 1 is an exemplary two-dimensional schematic illustration of an embodiment of a micelle α or β.
Figure 2:
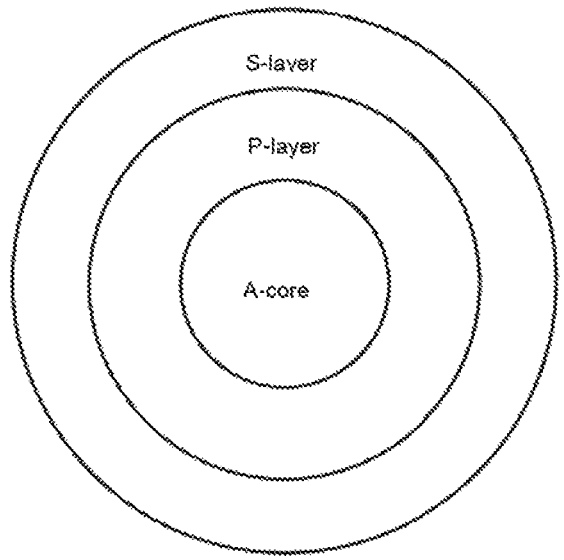
FIG. 2 an exemplary two-dimensional schematic illustration of an embodiment of a micelle α2 or β2.

FIGS. 1 and 2 are two-dimensional schematic illustrations of embodiments of micelles α and β.

In FIGS. 1 and 2, the A-core is an anionic or cationic micelle composed of ingredient molecules; the P-layer is formed from protecting agent molecules surrounding the A-core; and the A-core and the P-layer constitute a micelle α or a micelle β as a whole.

In the case where FIG. 1 is an illustration of the micelle α, the anionic micelle (hereinafter also called A-core) surface, namely, an anionized functional group of the anionic micelle, is negatively charged. The protecting agent molecule in the protecting agent-containing layer (hereinafter also called P-layer) has an atom bound to the A-core surface, namely, an anionized functional group of the anionic micelle, and the electron density of said atom is smaller than the electron density of the A-core surface, namely, the anionized functional group of the anionic micelle. Between said atom in the protecting agent molecule and the A-core surface, namely, the anionized functional group of the anionic micelle, an intermolecular interaction (e.g., hydrogen bond) is formed.

In the case where FIG. 1 is an illustration of the micelle β, the cationic micelle (hereinafter also called A-core) surface, namely, a cationized functional group of the cationic micelle, is positively charged. The protecting agent molecule in the protecting agent-containing layer (hereinafter also called P-layer) has an atom bound to the A-core surface, namely, a cationized functional group of the cationic micelle, and the electron density of said atom is greater than the electron density of the A-core surface, namely, the cationized functional group of the cationic micelle. Between said atom in the protecting agent molecule and the A-core surface, namely, the cationized functional group of the cationic micelle, an intermolecular interaction (e.g., cation-π Interaction) is formed.

In the case where the anionic micelle or the cationic micelle is protected by the protecting agent in which a hydrophobic functional group is exposed on the outer surface of the protecting agent-containing layer, a surfactant may be additionally present and in contact with the outer surface of the protecting agent-containing layer. The surfactant is present in the S-layer represented in FIG. 2. The additional presence of the surfactant in contact with the outer surface of the protecting agent-containing layer can further increase the hydrophilicity of the micelle α or β. The surfactant is preferably a compound having a long-chain alkyl group (e.g., an alkyl group of 7 or 8 or more carbon atoms). Specific examples of the surfactant include polysorbate 80 (TO-10M), polyoxyethylene hydrogenated castor oil (HCO60), polyethylene glycol monostearate (MYS-40), macrogol (PEG400), macrogol (PEG4000), and macrogol (PEG6000).

In other words, FIG. 2 shows a micelle α2 or β2, in which a surfactant is additionally present and in contact with the outer surface of the protecting agent-containing layer of the micelle α or β.

In the case where FIG. 2 is an illustration of the micelle α2, the anionic micelle (hereinafter also called A-core) surface, namely, an anionized functional group of the anionic micelle, is negatively charged. The protecting agent molecule in the protecting agent-containing layer (hereinafter also called P-layer) has an atom bound to the A-core surface, namely, an anionized functional group of the anionic micelle, and the electron density of said atom is smaller than the electron density of the A-core surface, namely, the anionized functional group of the anionic micelle. Between said atom in the protecting agent molecule and the A-core surface, namely, the anionized functional group of the anionic micelle, an intermolecular interaction (e.g., hydrogen bond) is formed.

In FIG. 2, the S-layer is illustrated as a layer in contact with the outer surface of the P-layer and is composed of surfactant molecules. The surfactant molecule in the S-layer is bound to a substituent, such as a hydrophobic substituent, of the protecting agent molecule present in the P-layer via an intermolecular interaction (e.g., van der Waals force etc.). Such an intermolecular interaction is formed at multiple sites on the outer surface of the P-layer, which underlies the formation of the surfactant-containing S-layer in contact with the outer surface of the P-layer.

In the case where FIG. 2 is an illustration of the micelle β2, the cationic micelle (hereinafter also called A-core) surface, namely, a cationized functional group of the cationic micelle, is positively charged. The protecting agent molecule in the protecting agent-containing layer (hereinafter also called P-layer) has an atom bound to the A-core surface, namely, a cationized functional group of the cationic micelle, and the electron density of said atom is greater than the electron density of the A-core surface, namely, the cationized functional group of the cationic micelle. Between said atom in the protecting agent molecule and the A-core surface, namely, the cationized functional group of the cationic micelle, an intermolecular interaction (e.g., cation-π interaction) is formed.

In FIG. 2, the S-layer is illustrated as a layer in contact with the outer surface of the P-layer and is composed of surfactant molecules. The surfactant molecule in the S-layer is bound to a substituent, such as a hydrophobic substituent, of the protecting agent molecule present in the P-layer via an intermolecular interaction (e.g., van der Waals force etc.). Such an intermolecular interaction is formed at multiple sites on the outer surface of the P-layer, which underlies the formation of the surfactant-containing S-layer in contact with the outer surface of the P-layer.

Micelle α
Ingredient

The ingredient in the micelle α is an ingredient that has a functional group capable of being anionized under basic conditions and has anionic micelle-forming ability. The ingredient in the micelle α preferably has a functional group capable of being anionized, for example, at mere than pH 7 but not exceeding 14, pH 3 to 14, pH 9 to 14, pH 10 to 14, pH 11 to 14, pH 12 to 14, or pH 13 to 14, and more preferably has a functional group capable of being anionized at pH 12 to 14 or pH 13 to 14.

Examples of the functional group capable of being anionized under basic conditions include a carboxyl group (—COOH), a sulfo group (—SO$_2$H), a phosphoryl group (—O—PO(OH)OH), a hydroxyl group (—OH), and a sulfonamide.

The functional group capable of being anionized under basic conditions may be anionized under acidic conditions (e.g., at less than pH 7, pH 6 or less, pH 5 or less, or the like).

The ingredient in the micelle α may have or not have a functional group capable of being cationized under acidic conditions, in addition to the functional group capable of being anionized under basic conditions.

Since one of the objects of the present invention is to solubilize a sparingly water-soluble ingredient, the ingredient in the micelle α is usually an ingredient with a low water solubility. In the production of pharmaceuticals such as solutions using the technology of the present invention, an ingredient with a low water solubility in a neutral pH range of 6 to 8 can be used as the ingredient in the micelle α. In the pharmaceutical field, the pH of solutions during long-term storage and in use is sometimes required to be near-neutral to avoid the risk of irritant reactions etc. as described below. In such an application, the effects of the present invention can be particularly preferably utilized. The ingredient with a low water solubility in a neutral pH range of 6 to 8 is preferably an ingredient having a solubility in water (e.g., 20° C.) of 1 g or less/100 g H$_2$O, more preferably 0.1 g or less/100 g H$_2$O, still more preferably 0.001 g or less/100 g H$_2$O in a neutral pH range of 6 to 8. In addition, the ingredient with a low water solubility in a neutral pH range of 6 to 8 may be an active pharmaceutical ingredient described as poorly water-soluble in an official compendium, such as the Japanese Pharmacopoeia, 17th edition.

The term "long-term storage" in the present disclosure may be 1-week storage, more preferably 2-week storage, and still more preferably 4-week storage after the production of solutions. The storage temperature during the storage period may be 40° C. or 25° C.

The following compounds are examples of the ingredient in the micelle α.

TABLE 1

| Generic name | Chemical name | Structure formula |
| --- | --- | --- |
| Fexofenadine hydrochloride | 2-(4-{(1RS)-1-Hydroxy-4-[4-(hydroxy-diphenylmethyl)piperidin-1-yl]butyl}phenyl)-2-methylpropanoic acid monohydrocloride | |

TABLE 1-continued

| Generic name | Chemical name | Structure formula |
| --- | --- | --- |
| Rebamipide | (2RS)-2-(4-Chlorobenzoylamino)-3-(2-oxo-1,2-dihydroquinolin-4-yl)propanoic acid | and its enantiomer |
| Indomethacin | [1-(4-Chlorobenzoyl)-5-methoxy-2-methyl-1H-indol-3-yl] acetic acid | |
| L-carbocysteine | (2R)-2-Amino-3-carboxymethylsulfanyl-propanoic acid | |
| Ibuprofen | (2RS)-2-[4-(2-Methylpropyl)phenyl] propanoic acid | and its enantiomer |
| Ursodeoxycholic acid | 3α,7β-Dihydroxy-5β-cholan-24-oic acid | |

Anionic Micelle

The anionic micelle refers to a micelle which is formed from ingredient molecules having a functional group capable of being anionized under basic conditions and has negatively-charged functional groups located on the surface. The anionic micelle corresponds to the A-core in the schematic illustration of FIG. 1 or 2.

Figure 3:
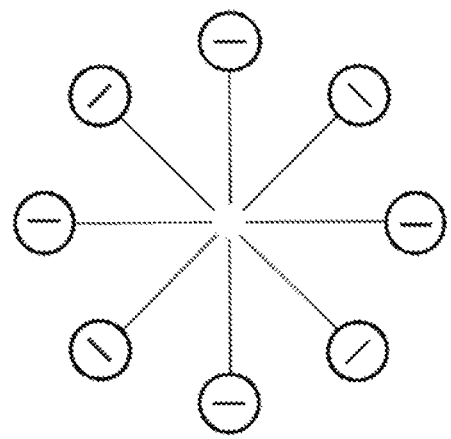
FIG. 3 is an exemplary schematic illustration of an anionic micelle.

FIG. 3 is a schematic illustration of an embodiment of the anionic micelle formed from, as a structural unit, an ingredient having a functional group capable of being anionized under basic conditions. The negative charge in FIG. 3 represents an anionized portion of the functional group capable of being anionized under basic conditions. The straight line bound to the negative charge in FIG. 3 is a simplified representation of the ingredient except for the anionized portion of the functional group capable of being anionized under basic conditions. That is, one unit consisting of the negative charge and the straight line bound thereto in FIG. 3 represents one unit of ingredient having a functional group capable of being anionized under basic conditions. In other words, the ingredient having a functional group capable of being anionized under basic conditions is a structural unit of the anionic micelle. In addition, two or more types of structural units may be present, two or more types of micelles consisting of the same structural unit may be present, and two or more types of structural units may compose one type of micelle or two or more types of micelles.

Micelle formation is generally known to have two different types, i.e., H-aggregate formation and J-aggregate formation. H-aggregates are formed by face-to-face parallel stacking of individual structural units. J-aggregates are formed by slipped (staggered) stacking of individual structural units in a head-to-tail orientation. In the present invention, the anionic micelle is preferably a J-aggregate as shown in FIG. 3. As J-aggregate formation occurs, the absorption spectrum in the ultraviolet to visible region shifts toward a longer wavelength as compared to that observed in monomeric dispersion of individual structural units. J-aggregate formation can be confirmed based on such a shift.

Protecting Agent

For some types of ingredients, their solubility is sufficiently increased by formation of the above-described anionic micelle and the formed anionic micelle is stable, but for others, the anionic micelle may have an insufficient stability. In particular, in the case where a solution containing the anionic micelle of the present invention is adjusted back to a near-neutral pH before long-term storage, the anionic micelle may disintegrate in the near-neutral pH range. In such a case, addition of a protecting agent can prevent the anionic micelle from disintegrating.

The protecting agent refers to a substance that binds to the anionic micelle via some kind of chemical bond and protects the anionic micelle. Specifically, the protecting agent is preferably capable of stabilizing the anionic micelle in water.

The protecting agent preferably has a hydroxy group (—OH) in water. The number of hydroxy groups (—OH) per molecule in water is preferably one or more, and more preferably 2, 3, 4, 5, 6, 7, or 8 or more.

Figure 4:
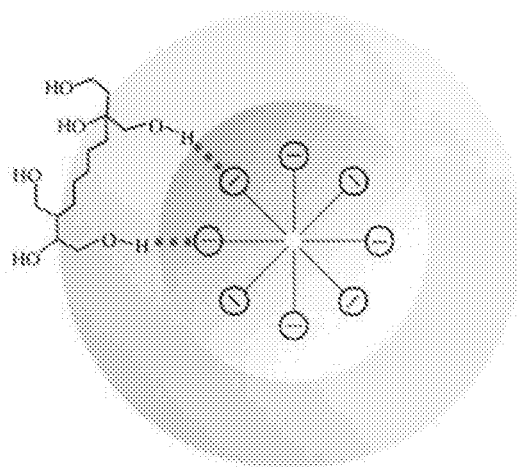
FIG. 4 is a schematic illustration of an embodiment of a micelle α.

The protecting agent, preferably has two or more hydroxy groups (—OH) in water and preferably has one or more linear, branched, or cyclic molecular skeletons between two or more hydroxy groups each bound to an anionized functional group of the anionic micelle via a chemical bond (e.g., hydrogen bond) (see FIG. 4 as an example). The number of elements in the molecular skeleton between two or more hydroxy groups each bound to the anionic micelle via a chemical bond (e.g., hydrogen bond) is preferably one or more, and more preferably 2, 3, 4, 5, 6, 7, or 8 or more. In the case where two or more molecular skeletons are present between the two or more hydroxy groups each bound to an anionized functional group of the anionic micelle via a chemical bond (e.g., hydrogen bond), two or more protecting agent molecules having a molecular skeleton described above may be bound to each other via a chemical bond (e.g., hydrogen bond) (see FIGS. 5 and 6 as examples).

Examples of such a protecting agent include water-soluble polymers, polyalcohols, sugar alcohols, etc. Particularly preferred are water-soluble polymers.

Specific examples of the protecting agent include polyethylene glycol, glycerin, propylene glycol, sorbitol (e.g., D-sorbitol etc.), mannitol, N-acetylglucosamine, chondroitin sulfate, glycyrrhizic acid, dipotassium glycyrrhizinate, hydroxypropylmethyl cellulose, methylcellulose (e.g., methylcellulose 15, methylcellulose 400, etc.), carboxymethyl cellulose, sodium carboxymethylcellulose, povidone (e.g., povidone K30 etc.), polyoxyethylene hydrogenated castor oil, polysorbate 80, macrogol (e.g., PEG400, PEG4000, PEG6000, etc.), and any combination thereof.

Relation Between Protecting Agent and Anionic Micelle

Figure 5:
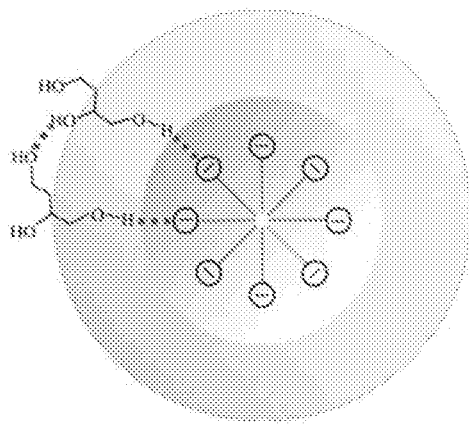
FIG. 5 is a schematic illustration of an embodiment of a micelle α.
Figure 6:
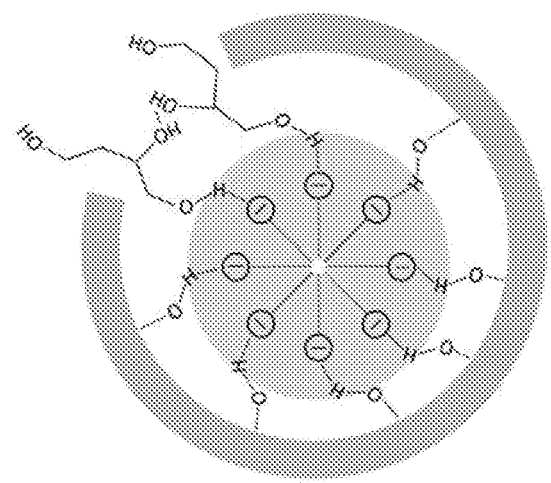
FIG. 6 is a schematic illustration of an embodiment of a micelle α.

FIGS. 4 to 6 are schematic illustrations of embodiments of the micelle α, but the micelle α is not limited thereto.

In FIG. 4, the surface of the anionic micelle represented as the area outlined by the inner boundary is negatively charged. The protecting agent molecule (one molecule is shown as a representative example in the protecting agent-containing layer represented as the area between the inner and outer boundaries) has a hydrogen atom bound to anionized functional group of the anionic micelle, and the electron density of said hydrogen atom is smaller than the electron density of the anionized functional group of the anionic micelle. Between said hydrogen atom and the anionized functional group of the anionic micelle, a chemical bond (e.g., hydrogen bond) is formed. That, is, each dotted line in FIG. 4 represents the chemical bond (e.g., hydrogen bond).

In FIG. 5, the surface of the anionic micelle represented as the area outlined by the inner boundary is negatively charged. The protecting agent molecule (two molecules are shown as representative examples in the protecting agent-containing layer represented as the area between the inner and outer boundaries) has a hydrogen atom bound to an anionized functional group of the anionic micelle, and the electron density of said hydrogen atom is smaller than the electron density of the anionized functional group of the anionic micelle. Between said hydrogen atom and the anionized functional group of the anionic micelle, a chemical bond (e.g., hydrogen bond) is formed. In addition, the two protecting agent molecules are bound to each other via a chemical bond (e.g., hydrogen bond). That is, each dotted line in FIG. 5 represents the chemical bond (e.g., hydrogen bond).

FIG. 6 is a detailed illustration of the chemical bond between the protecting agent and the anionic micelle in the micelle that is the same as the micelle α of FIG. 5.

The protecting agent has an atom bound to an anionized functional group of the anionic micelle, and the electron density of said atom is preferably smaller than the electron density of the anionized functional group of the anionic micelle.

The bond formed between said atom in the protecting agent and the anionized functional group of the anionic micelle is preferably a chemical bond, such as a hydrogen bond, a covalent bond, a bond by van der Waals force, or an ionic bond, and more preferably a hydrogen bond.

Physical Properties and Characteristics of Micelles

The physical properties of micelles can be examined by measuring the particle size distribution of the micelles by a known method. Regarding the micelle α of the present invention, the diameter of the micelle α is larger than the diameter of the anionic micelle as measured. The diameter of the anionic micelle varies greatly with the molecular weight, the concentration, etc. of the ingredient, but is usually 0.1 nm to 100 nm, particularly preferably 1 nm to 10 nm. The diameter of the micelle α is usually 0.2 nm to 150 nm, and particularly preferably 1.5 nm to 20 nm.

The presence of the micelle α can be confirmed by any of the following exemplary procedures. In one example, a large amount of counterions (cations) (e.g., sodium chloride) is added to a micelle α-containing aqueous solution to cancel negative charges, and the precipitation of the ingredient is checked. Alternatively, an inorganic salt (e.g., sodium chloride) is added to a micelle α-containing aqueous solution to reduce the critical micelle concentration (CMC), and the precipitation of the ingredient is checked.

Solution

The present invention provides a micelle α-containing solution in which an ingredient having a functional group capable of being anionized under basic conditions is solubilized. The lower limit of the concentration of the micelle α in the solution of the present invention is not particularly limited, and the concentration of the ingredient, (not a salt) is, for example, 0.01% (w/v) or more, 0.02% (w/v) or more, 0.03% (w/v) or more, 0.04% (w/v) or more, 0.05% (w/v) or more, 0.07% (w/v) or more, 0.09% (w/v) or more, 0.1% (w/v) or more, or 0.2% (w/v) or more. The upper limit of the concentration of the micelle α in the solution of the present invention is not particularly limited, and the concentration of the ingredient (not a salt) is, for example, 5.0% (w/v) or less, 3.0% (w/v) or less, 1.0% (w/v) or less, 0.5% (w/v) or less, 0.3% (w/v) or less, 0.25% (w/v) or less, 0.2% (w/v) or Less, 0.15% (w/v) or less, or 0.1% (w/v) or less. All the combinations of the above-listed lower limit concentrations and upper limit concentrations are included in the present invention. The concentration of the micelle α can be easily adjusted in any step of the production method described later.

The pH of the solution of the present invention during long-term storage is not particularly limited and may be near-neutral to near-acidic, near-neutral to near-basic, near-neutral to near-weakly acidic, near-neutral to near-weakly basic, or the like. Preferred is a near-neutral pH. The "near-neutral pH" in this context is, for example, pH 5 to 9, pH 5.5 to 3.5, pH 6 to 8, pH 6.5 to 7.5, or the like. The pH adjustment is performed according to a known method (e.g., addition of hydrochloric acid, sulfuric acid, nitric acid, or the like). Since the sparingly water-soluble ingredient in the solution of the present invention is maintained in a soluble state even at a near-neutral pH, the solution of the present invention is useful, in particular as an eye drop, a nasal drop, or an oral solution. In the case where the solution of the present invention is used as an eye drop, a nasal drop, or an oral solution, the daily dose for an adult, may be 0.01 to 10000 mg in terms of the ingredient (not a salt). In the case where the solution of the present invention is used as an oral solution, the daily dose for an adult may be 1 to 10000 mg, 0.1 to 1000 mg, or 1 to 100 mg in terms of the ingredient (net a salt). The daily dose may be given as a single dose or in divided doses.

In the case where the ingredient having a functional group capable of being anionized under basic conditions is a bioactive ingredient or an active pharmaceutical ingredient, the solution of the present invention can exert the bioactivity or pharmaceutical activity of the ingredient. In the case where the ingredient is useful for the prevention and/or treatment of pruritus associated with allergic rhinitis, urticaria, and skin disease (eczema and dermatitis, cutaneous pruritus, atopic dermatitis), the solution of the present invention is useful for the prevention and/or treatment of pruritus associated with allergic rhinitis, urticaria, and skin disease (eczema and dermatitis, cutaneous pruritus, atopic dermatitis).

Production Method

The present invention provides a production method of a micelle α, the micelle α comprising an anionic micelle and a protecting agent, the anionic micelle being formed from, as a structural unit, an ingredient having a functional group capable of being anionized under basic conditions, the protecting agent protecting the anionic micelle, the production method comprising the following steps (A) and (B):
(A) suspending, in water, the ingredient having a functional group capable of being anionized under basic conditions, and subsequently basifying the resulting suspension; and
(B) adding the protecting agent.

In the production method of the micelle α, an exemplary procedure in step (A) (the step of suspending, in water, the ingredient having a functional group capable of being anionized under basic conditions, and subsequently basifying the resulting suspension) is as follows. The ingredient and water are mixed at a desired ratio and stirred in the usual manner, and a base is added to the resulting suspension for basification. The concentration of the ingredient in the suspension is preferably a critical micelle concentration (CMC) or higher. The ratio of the ingredient and the water (ingredient (g):water (mL)) can be changed as appropriate for the ingredient and may be specifically 0.001:100 to 5:100, 0.01:100 to 3:100, 0.1:100 to 1:100, or the like. The basic range in this context may be changed as appropriate for the ingredient, but is preferably a pH range in which the ingredient is dissolved fully or in part (e.g., 50% or more, 60% or more, 70% or more, 60% or mere, or 90% or more), specifically, pH 9 to 14, pH 10 to 13, pH 11 to 13, pH 11.5 to 13, pH 11.7 to 12.9, or the like. In the case where the ingredient is fexofenadine, the pH is preferably 12 or more. The base used for pH adjustment may be a strong base (e.g., sodium hydroxide, potassium hydroxide, barium hydroxide, calcium hydroxide, etc.) or a weak base (e.g., ammonia, trometamol, etc.), but preferred is a strong base.

In the production method of the micelle α, in the step (B) of adding the protecting agent, a desired amount of the protecting agent is added to the ingredient-containing composition obtained in step (A). The molar ratio of the ingredient and the protecting agent (ingredient:protecting agent) can be changed as appropriate for the protecting agent and may be, for example, 100:1 to 1:100.

The micelle α produced through the above steps (A) and (B) is sufficiently stable and can be used without further modification. However, in the case where the present invention is applied to, for example, pharmaceuticals, a micelle α-containing solution of an unmodified pH is too irritant for use in humans and is sometimes hard to use practically. In such a case, the production method of the micelle α may comprise a step (C) of adjusting the pH to fall within a range acceptable for human application after step (B).

In the step (C) of adjusting the pH to fall within a range acceptable for human application, a pH adjuster, a pH buffering agent, or the like is added to the ingredient-containing composition obtained in step (B) to adjust the pH of the composition to fall within a range acceptable for human application. Examples of the pH adjuster or the pH buffering agent include hydrochloric acid, citric acid and phosphoric acid, and salts thereof, etc. The range acceptable for human application refers to, for example, a range acceptable for ocular or nasal administration, oral administration in the form of a solution, etc. to humans. In this context, the range acceptable for human application is, for example, pH 5 to 9, preferably pH 6 to 8, and more preferably pH 6 to 7, pH 7 to 8, or the like.

Advantageously, the micelle α produced through the above steps including (A) and (B), even after such pH adjustment to a range acceptable for human application, does not disintegrate easily and can exert the effects of the present, invention.

Micelle Produced by the Above Production Method

The present invention provides a micelle (also called a micelle α) produced by the above production method, the micelle comprising an anionic micelle and a protecting agent, the anionic micelle being formed from, as a structural unit, an ingredient having a functional group capable of being anionized under basic conditions, the protecting agent protecting the anionic micelle. For the micelle α, see the above description of the micelle α.

Method for Increasing the Solubility of the Ingredient

The present invention provides a method for increasing the solubility of an ingredient having a functional group capable of being anionized under basic conditions, the method comprising a step of forming an anionic micelle from the ingredient having a functional group capable of being anionized under basic conditions. The solubility of the ingredient, having a functional group capable of being anionized under basic conditions refers to a solubility of the ingredient at a near-neutral pH (e.g., pH 6 to 8, pH 6.5 to 7.5, etc.). The method for increasing the solubility of an ingredient having a functional group capable of being anionized under basic conditions preferably further comprises a step of protecting the anionic micelle with a protecting agent.

Use

The present invention includes use of a micelle α for production of a solution in which an ingredient having a functional group capable of being anionized under basic conditions is dissolved at high concentration.

Micelle β

Ingredient

The ingredient has a functional group capable of being cationized under acidic conditions.

The ingredient in the micelle β has a functional group capable of being cationized under acidic conditions. The ingredient in the micelle β preferably has a functional group capable of being cationized, for example, at pH 1 or more but less than pH 7, pH 1 to 6, pH 1 to 5, pH 1 to 4, pH 1 to 3, pH 1 to 2.5, or pH 1 to 2, and more preferably has a functional group capable of being cationized at pH 1 to 2.5 or pH 1 to 2.

Examples of the functional group capable of being cationized under acidic conditions include an amino group, a monomethylamino group, a dimethylamino group, a monoethylamino group, a diethylamino group, a morpholino group, a piperidino group, etc.

The functional group capable of being cationized under acidic conditions may be cationized under basic conditions (e.g., at more than pH 7, pH 3 or more, pH 9 or more, or the like).

The ingredient in the micelle β may have or not have a functional group capable of being anionized under basic conditions, in addition to the functional group capable of being cationized under acidic conditions. The ingredient with a low water solubility in a neutral pH range of 6 to 8 is preferably an ingredient having a solubility in water (e.g., 20° C.) of 1 g or less/100 g $H_2O$, more preferably 0.1 g or less/100 g $H_2O$, still more preferably 0.001 g or less/100 g $H_2O$ in a neutral pH range of 6 to 8. In addition, the ingredient with a low water solubility in a neutral pH range of 6 to 8 may be an active pharmaceutical ingredient described as poorly water-soluble in an official compendium, such as the Japanese Pharmacopoeia, 17th edition.

The term "long-term storage" in the present disclosure may be 1-week storage, more preferably 2-week storage, and still more preferably 4-week storage after the production of solutions. The storage temperature during the storage period may be 40° C. or 25° C.

The following compounds are examples of the ingredient in the micelle β.

TABLE 2

| Generic name | Chemical name | Structural formula |
| --- | --- | --- |
| Brinzolamide | (R)-4-(Ethylamino)-3,4-dihydro-2-(3-methoxypropyl)-2H-thieno[3,2,e]-1,2-thiazine-6-sulfonamide 1,1-dioxide | |
| Trimebutine maleate | (2RS)-2-Dimethylamino-2-phenyl butyl 3,4,5-trimethoxybenzoate monomaleate | and its enantiomer |
| Ethyl aminobenzoate | Ethyl 4-aminobenzoate | |
| Baclofen | (3RS)-4-Amino-3-(4-chlorophenyl) butanoic acid | and its enantiomer |

TABLE 2-continued

| Generic name | Chemical name | Structural formula |
| --- | --- | --- |
| Metoclopramide | 4-Amino-5-chloro-N-[2-(diethyl-amino)ethyl]-2-methoxybenzamide | |
| Lidocaine hydrochloride | 2-Diethylamino-N-(2,6-dimethylphenyl)acetamide hydrochloride | |

Cationic Micelle

The cationic micelle refers to a micelle which is formed from ingredient molecules having a functional group capable of being cationized under acidic conditions and has positively-charged functional groups located on the surface. The cationic micelle corresponds to the A-core in the schematic illustration of FIG. 1 or 2.

Figure 7:
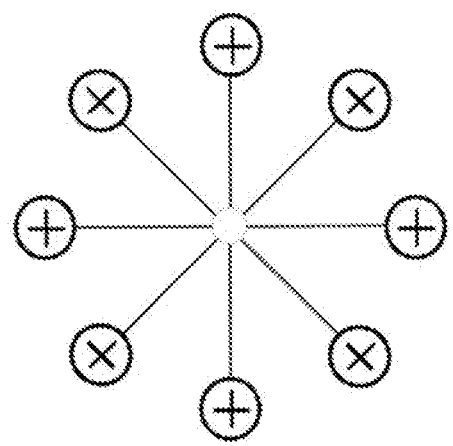
FIG. 7 is an exemplary schematic illustration of a cationic micelle.

FIG. 7 is a schematic illustration of an exemplary cationic micelle β. The positive charge in FIG. 7 represents a cationized portion of the functional group capable of being cationized under acidic conditions. The straight line bound to the positive charge in FIG. 7 is a simplified representation of the ingredient except for the cationized portion of the functional group capable of being cationized under acidic conditions. That is, one unit consisting of the positive charge and the straight line bound thereto in FIG. 7 represents one unit of ingredient having a functional group capable of being cationized under acidic conditions. In other words, the ingredient having a functional group capable of being cationized under acidic conditions is a structural unit of the cationic micelle. In addition, two or more types of structural units may be present. In this case, two or more types of micelles consisting of the same structural unit may be present, and two or more types of structural units may compose one type of micelle or two or more types of micelles.

Micelle formation is generally known to have two different types, i.e., H-aggregate formation and J-aggregate formation. H-aggregates are formed by face-to-face parallel stacking of individual structural units. J-aggregates are formed by slipped (staggered) stacking of individual structural, units in a head-to-tail orientation. In the present invention, the cationic micelle is preferably a J-aggregate as shown in FIG. 7. As J-aggregate formation occurs, the absorption spectrum in the ultraviolet to visible region shifts toward a longer wavelength as compared to that observed in monomeric dispersion of individual structural units. J-aggregate formation can be confirmed based on such a shift.

Protecting Agent

For some types of ingredients, their solubility is sufficiently increased by formation of the above-described cationic micelle and the formed cationic micelle is stable, but for others, the cationic micelle may have an insufficient stability. In particular, in the case where a solution containing the cationic micelle of the present invention is adjusted back to a near-neutral pH before long-term storage, the cationic micelle may disintegrate in the near-neutral pH range. In such a case, addition of a protecting agent can prevent the cationic micelle from disintegrating.

The protecting agent may be any substance that protects the cationic micelle, and specifically, the protecting agent is preferably capable of stabilizing the cationic micelle in water.

The protecting agent preferably has a π electron in water. A π electron is an electron which is involved in a π bond and present in a p orbital. A partial negative charge due to the π electron in the p orbital extending along the z axis in the positive and negative directions generates dipoles, but due to the symmetry of the p orbital along the z orbital, the dipoles cancel out and the net dipole moment is zero. However, the partial negative charge induces a counterbalancing charge, which generates other dipoles, resulting in an electric quadrupole. The electric quadrupole moment drives an intermolecular interaction with a cation. The intermolecular interaction between the π electron and the cation (cation-π interaction) is a noncovalent intermolecular interaction, and the energy of the interaction is equal to that of a hydrogen bond. The protecting agent preferably has an intermolecular interaction with the surface of the cationic micelle (e.g., cation-π interaction) (see FIG. 8 as an example).

Such a protecting agent is preferably, for example, a compound having a stable π electron. Specifically, the protecting agent is preferably a compound having a phenyl group as a substituent, a phenyl derivative, or the like.

Examples of the protecting agent include compounds having 1 to 10 benzene rings each optionally having a substituent (each substituent may be the same or different and is —O($C_2H_4$O)mH (wherein m represents an integer of 8 to 10) or a ($C_{1-10}$) alkyl group (wherein the ($C_{1-10}$) alkyl group represents a straight-chain or branched-chain alkyl group of 1 to 10 carbon atoms, such as a methyl group, an ethyl group, a n-propyl group, an isopropyl group, a n-butyl group, an isobutyl group, a sec-butyl group, a tert-butyl group, a n-pentyl group, an isopentyl group, a tert-pentyl group, a neopentyl group, a 2,3-dimethylpropyl group, a 1-ethylpropyl group, a 1-methylbutyl group, a 2-methylbutyl group, a n-hexyl group, an isohexyl group, a 2-hexyl group, a 3-hexyl group, a 2-methylpentyl group, a 3-methylpentyl group, a 1,1,2-trimethylpropyl group, a 3,3-dimethylbutyl group, a n-heptyl group, a n-octyl group, a n-nonyl group, and a n-decyl group)).

In addition, the protecting agent is exemplified by tyloxapol, a compound represented by the following general formula (I):

[Chem. 1]

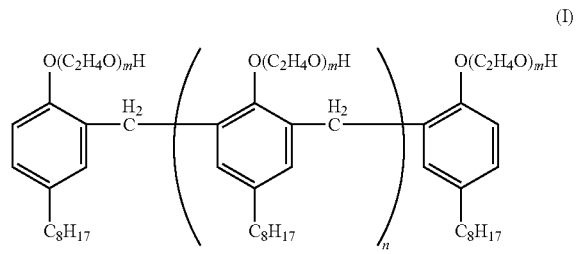

(I)

(wherein m represents an integer of 8 to 10, and n represents an Integer of 1 to 5).

Relation Between Protecting Agent and Cationic Micelle

Figure 8:
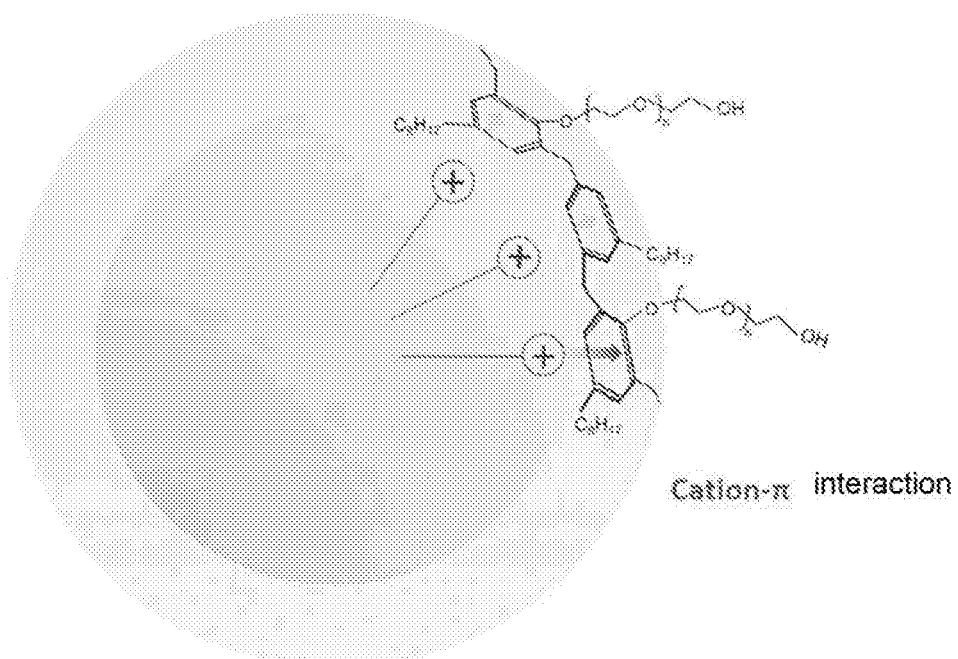
FIG. 8 is a schematic illustration of an embodiment of a micelle β.

FIG. 8 is a schematic illustration of an embodiment of the micelle β, but the micelle β is not limited thereto.

In FIG. 8, the surface of the cationic micelle represented as the area outlined by the inner boundary is positively charged The protecting agent, molecule (one molecule is shown as a representative example in the protecting agent-containing layer represented as the area between the inner and outer boundaries) has a benzene ring bound to a cationized functional group present in the cationic micelle, and the electron density of said benzene ring is greater than the electron density of the cationic micelle surface. Between said benzene ring and the cationic micelle surface, an intermolecular interaction (e.g., cation-π interaction) is formed. That is, the arrow (→) in FIG. 8 represents the intermolecular interaction (e.g., cation-π interaction).

Physical Properties and Characteristics of Micelle

The physical properties of micelles can be examined by measuring the particle size distribution of the micelles by a known method. Regarding the micelle β of the present invention, the diameter of the micelle β is larger than the diameter of the cationic micelle as measured. The diameter of the cationic micelle varies greatly with the molecular weight, the concentration, etc. of the ingredient, but is usually 0.1 nm to 100 nm, particularly preferably 1 nm to 10 nm. The diameter of the micelle β is usually 0.2 nm to 150 nm, and particularly preferably 1.5 nm to 20 nm.

The presence of the micelle β can be confirmed by any of the following exemplary procedures. In one example, a large amount of counterions (anions) (e.g., sodium chloride) is added to a micelle β-containing aqueous solution to cancel positive charges, and the precipitation of the ingredient is checked. Alternatively, an inorganic salt (e.g., sodium chloride) is added to a micelle β-containing aqueous solution to reduce the critical micelle concentration (CMC), and the precipitation of the ingredient is checked.

Solution

The present invention provides a micelle β-containing solution in which an ingredient having a functional group capable of being cationized under acidic conditions is solubilized. The lower limit of the concentration of the micelle β in the solution of the present invention is not particularly limited, and the concentration of the ingredient (not a salt) is, for example, 0.01% (w/v) or more, 0.02% (w/v) or more, 0.03% (w/v) or more, 0.04% (w/v) or more, 0.05% (w/v) or more, 0.07% (w/v) or more, 0.09% (w/v) or more, 0.1% (w/v) or more, or 0.2% (w/v) or more. The upper limit of the concentration of the micelle β in the solution of the present invention is not particularly limited, and the concentration of the ingredient (not a salt) is, for example, 5.0% (w/v) or less, 3.0% (w/v) or less, 1.0% (w/v) or less, 0.5% (w/v) or less, 0.3% (w/v) or less, 0.25% (w/v) or less, 0.2% (w/v) or less, 0.15% (w/v) or less, or 0.1% (w/v) or less. All the combinations of the above-listed lower limit concentrations and upper limit concentrations are included In the present invention. The concentration of the micelle β can be easily adjusted in any step of the production method described later.

The pH of the solution of the present invention during long-term storage is not particularly limited, and may be near-neutral to near-acidic, near-neutral to near-basic, near-neutral to near-weakly acidic, near-neutral to near-weakly basic, or the like. Preferred is a near-neutral pH. The "near-neutral pH" in this context is, for example, pH 5 to 9, pH 5.5 to 8.5, pH 6 to 8, pH 6.5 to 7.5, or the like. The pH adjustment is performed according to a known method (e.g., addition of sodium hydroxide, potassium hydroxide, or the like). Since the sparingly water-soluble ingredient, in the solution of the present invention is maintained in a soluble state even at a near-neutral pH, the solution of the present invention is useful, in particular as an eye drop, a nasal drop, or an oral solution. In the case where the solution of the present invention is used as an eye drop, a nasal drop, or an oral solution, the daily dose for an adult may be 0.01 to 10000 mg in terms of the ingredient (not a salt). In the case where the solution of the present invention is used as an oral solution, the daily dose for an adult may be 1 to 10000 mg, 0.1 to 1000 mg, or 1 to 100 mg in terms of the ingredient (not a salt). The daily dose may be given as a single dose or in divided doses.

In the case where the ingredient having a functional group capable of being cationized under acidic conditions is a bioactive ingredient or an active pharmaceutical ingredient, the solution of the present invention can exert the bioactivity or pharmaceutical activity of the ingredient. In the case where the ingredient is useful for the prevention and/or treatment of pruritus associated with allergic rhinitis, urticaria, and skin disease (eczema and dermatitis, cutaneous pruritus, atopic dermatitis), the solution of the present invention is useful for the prevention and/or treatment of pruritus associated with allergic rhinitis, urticaria, and skin disease (eczema and dermatitis, cutaneous pruritus, atopic dermatitis).

Production Method

The present invention provides a production method of a micelle β, the micelle β comprising a cationic micelle and a protecting agent, the cationic micelle being formed from, as a structural unit, an ingredient having a functional group capable of being cationized under acidic conditions, the protecting agent protecting the cationic micelle, the production method comprising the following steps (a) and (b): (a) suspending, in water, the ingredient having a functional group capable of being cationized under acidic conditions, and subsequently acidifying the resulting suspension; and (b) adding the protecting agent.

In the production method of the micelle β, an exemplary procedure in step (a) (the step of suspending, in water, the ingredient having a functional group capable of being cationized under acidic conditions, and subsequently acidifying the resulting suspension) is as follows. The ingredient and water are mixed at a desired ratio and stirred in the usual manner, and an acid is added to the resulting suspension for acidification. The concentration of the ingredient in the suspension is preferably a critical micelle concentration (CMC) or higher. The ratio of the ingredient and the water (ingredient (g):water (mL)) can be changed as appropriate for the ingredient and may be specifically 0.001:100 to 5:100, 0.01:100 to 3:100, 0.1:100 to 1:100, or the like. The acidic range in this context may be changed as appropriate for the ingredient, out is preferably a pH range in which the ingredient is dissolved fully or in part (e.g., 50% or more, 60% or more, 70% or more, 80% or more, or 90% or more), specifically, pH 1 or more but less than pH 7, pH 1 to 6, pH 1 to 5, pH 1 to 4, pH 1 to 3, pH 1 to 2.5, pH 1 to 2.2, or the like. In the case where the ingredient is brinzolamide, the pH is preferably an acidic range of 2 or less. The acid may be a strong acid (e.g., hydrochloric acid, sulfuric acid, nitric acid, hydrogen iodide, perchloric acid, hydrogen bromide, etc.) or a weak acid (e.g., citric acid, acetic acid, formic acid, oxalic acid, hydrogen sulfide, etc.), but preferred is a strong acid.

In the production method of the micelle β, in the step (b) of adding the protecting agent, a desired amount of the protecting agent is added to the ingredient-containing composition obtained in step (a). The molar ratio of the ingredient and the protecting agent (ingredient:protecting agent) can be changed as appropriate for the protecting agent and may be, for example, 100:1 to 1:1000.

For some types of protecting agents, a hydrophobic group in the protecting agent molecule is exposed on the outer surface of the micelle β, and for this reason, the solubility of the micelle β may fail to achieve the desired level. In such a case, the production method of the micelle β may comprise a step (c) of adding a surfactant concomitantly with or after step (b) as needed. In step (c), a desired amount of the surfactant is added to the ingredient-containing composition obtained in step (b). The molar ratio of the ingredient and the surfactant (ingredient:surfactant) can be changed as appropriate for the surfactant and may be, for example, 100:1 to 1:1000.

The micelle β produced through the above steps (a) and (b), or optionally the above steps (a), (b), and (c), is sufficiently stable and can be used without further modification. However, in the case where the present invention is applied to, for example, pharmaceuticals, a micelle β-containing solution of an unmodified pH is too irritant for use in humans and is sometimes hard to use practically. In such a case, the production method of the micelle β may comprise a step (d) of adjusting the pH to fall within a range acceptable for human application after step (b) or (c). In the case where the production method of the micelle β comprises step (d) after step (b), step (d) may precede step (c).

In the step (d) of adjusting the pH to fall within a range acceptable for human application, a pH adjuster, a pH buffering agent, or the like is added to the ingredient-containing composition obtained in step (b) or (c) to adjust the pH of the composition to fall within a range acceptable for human application. Examples of the pH adjuster or the pH buffering agent include hydrochloric acid, citric acid and phosphoric acid, and salts thereof, etc. The range acceptable for human application refers to, for example, a range acceptable for ocular or nasal administration, oral administration in the form of a solution, etc. to humans. In this context, the range acceptable for human application is, for example, pH 5 to 9, preferably pH 6 to 3, and more preferably pH 6 to 7, pH to 8, or the like.

Micelle Produced by the Above Production Method

The present invention provides a micelle (also called a micelle β) produced by the above production method, the micelle comprising a cationic micelle and a protecting agent, the cationic micelle being formed from, as a structural unit, an ingredient having a functional group capable of being cationized under acidic conditions, the protecting agent protecting the cationic micelle. For the micelle β, see the above description of the micelle β.

Method for Increasing the Solubility of the Ingredient.

The present invention provides a method for increasing the solubility of an ingredient having a functional group capable of being cationized under acidic conditions, the method comprising a step of forming a cationic micelle from the ingredient having a functional group capable of being cationized under acidic conditions. The solubility of the ingredient having a functional group capable of being cationized under acidic conditions may be a solubility of the ingredient at a near-neutral pH (e.g., pH 6 to 8, pH 6.5 to 7.5, etc.), a solubility of the ingredient at a near-basic pH (e.g., pH 8 to 14, pH 8 to 10, pH 8 to 9, etc.), or a solubility of the ingredient at a near-acidic pH (e.g., pH 3 to 6, pH 4 to 6, pH 5 to 6, etc.). The method for increasing the solubility of an ingredient having a functional group capable of being cationized under acidic conditions preferably further comprises a step of protecting the cationic micelle with a protecting agent.

Use

The present invention includes use of a micelle β for production of a solution in which an ingredient having a functional group capable of being cationized under acidic conditions is dissolved at high concentration.

EXAMPLES

Hereinafter, the present invention will be described in more detail by examples, but the present invention is not limited thereto. Many modifications can be made by persons of ordinary knowledge in the art; within the scope of the technical idea of the present invention. The "room temperature (RT)" in the tables given below means the "uncontrolled room temperature".

(1) Ingredient having a functional group capable of being anionized under basic conditions Test Example 1: Fexofenadine hydrochloride Fexofenadine-containing liquid compositions were produced by the procedure shown in Table 3 below. Solubilization of fexofenadine in each liquid composition was evaluated just after production and 1 to 4 weeks after production (conditions:uncontrolled room temperature, 5° C. or 40° C.) (Tables 4 to 6). In Tables 4 to 6, the circle symbol indicates that no precipitation was visually observed, the cross symbol indicates that precipitation was visually observed, and "-" indicates "not tested". In the case where precipitation was observed under certain conditions, the examination under the same conditions was discontinued.

TABLE 3

| Examples | Comparative Examples |
|---|---|
| 1) Prepare 40 mL of purified water, | 1) Prepare 40 mL of purified water. |
| 2) Add fexofenadine hydrochloride at a final concentration of 0.1 to 0.3% (w/v) (see Table 4, 5 or 7). | 2) Add fexofenadine hydrochloride at a final concentration of 0.1% (w/v). |

TABLE 3-continued

| Examples | Comparative Examples |
|---|---|
| 3) Adjust the pH to 12 to 13 with 1.0N sodium hydroxide. | 3) (This step is not performed in Comparative Example.) |
| 4) Add the indicated protecting agent (see Table 4, 5 or 7). | 4) Add the indicated protecting agent (see Table 6). |
| 5) Add water to a final volume of 50 mL. | 5) Add water to a final volume of 50 mL. |
| 6) Adjust the pH to near-neutral with hydrochloric acid or citric acid hydrate (see Table 4, 5 or 7). | 6) Adjust the pH to near-neutral with 1.0N sodium hydroxide. |

TABLE 4

Fexofenadine-containing compositions (1) produced by the procedure for Examples

| | | Production example | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Active ingredient | Fexofenadine hydrochloride | | | | | 0.1% | | | | | | | |
| Protecting agent | Glycerin | 2% | | | | | | | | | | | |
| | Mannitol | | | 1% | | | | | | | | | |
| | Dipotassium glycyrrhizinate | | | | | | 0.25% | | 1% | | | | |
| | Hydroxypropyl-methyl cellulose | | | | | | | | | | 0.3% | | |
| | Povidone K30 | | | | | | | | | | | | |
| | Methylcellulose 15 | | | | | | | | | | | | |
| | Methylcellulose 400 | | | | | | | | | | | | |
| | Sodium carboxy-methylcellulose | | | | | | | | | | | | |
| pH adjuster | Hydrochloric acid | q.s. | | q.s. | | q.s. | | q.s. | | q.s. | q.s. | | |
| | Citric acid hydrate | | q.s. | | q.s. | | q.s. | | q.s. | | | q.s. | q.s. |
| Evaluation of solubilization | pH of formulation | 5.89 | 5.85 | 6.02 | 6.05 | 6.02 | 6.09 | 5.97 | 5.76 | 7.07 | 6.02 | 5.74 | 6.5 |
| | Just after production | ○ | ○ | ○ | ○ | ○ | ○ | ○ | ○ | ○ | ○ | ○ | ○ |
| RT | 1 week after production | ○ | ○ | ○ | ○ | ○ | ○ | ○ | ○ | ○ | ○ | ○ | ○ |
| | 2 weeks after production | ○ | ○ | ○ | ○ | ○ | ○ | ○ | ○ | ○ | ○ | ○ | ○ |
| | 3 weeks after production | ○ | ○ | ○ | ○ | ○ | ○ | ○ | ○ | ○ | ○ | ○ | ○ |
| | 4 weeks after production | ○ | — | ○ | ○ | ○ | ○ | ○ | ○ | ○ | ○ | ○ | ○ |
| 5° C. | 1 week after production | ○ | — | ○ | ○ | ○ | ○ | ○ | ○ | ○ | ○ | ○ | ○ |
| | 2 weeks after production | ○ | — | ○ | ○ | ○ | ○ | ○ | ○ | ○ | ○ | ○ | ○ |
| | 3 weeks after production | ○ | — | ○ | ○ | ○ | ○ | ○ | ○ | ○ | ○ | ○ | ○ |
| | 4 weeks after production | ○ | — | — | — | ○ | ○ | ○ | ○ | ○ | ○ | ○ | ○ |
| 5° C. | 1 week after production | ○ | — | — | — | ○ | ○ | ○ | ○ | ○ | ○ | ○ | ○ |
| | 2 weeks after production | — | — | — | — | ○ | ○ | ○ | ○ | ○ | ○ | ○ | ○ |
| | 3 weeks after production | — | — | — | — | ○ | ○ | ○ | ○ | ○ | — | — | — |
| | 4 weeks after production | — | — | — | — | ○ | ○ | ○ | ○ | ○ | — | — | — |

| | | Production example | | | | | | | | | | |
|---|---|---|---|---|---|---|---|---|---|---|---|---|
| | | 13 | 14 | 15 | 16 | 17 | 18 | 19 | 20 | 21 | 22 | 23 |
| Active ingredient | Fexofenadine hydrochloride | | | | | 0.1% | | | | | | |
| Protecting agent | Glycerin | | | 2% | | | | | | | | |
| | Mannitol | | | | | | | | | | | |
| | Dipotassium glycyrrhizinate | | | | | | | | | | | |
| | Hydroxypropyl-methyl cellulose | | 0.3% | | | | | | | | | |
| | Povidone K30 | | | | | | | 2% | | | | |
| | Methylcellulose 15 | | | | | | | | | 0.5% | | |
| | Methylcellulose 400 | | | | | | | | | | | 0.5% |
| | Sodium carboxy-methylcellulose | | | | | | | | | | | |

TABLE 4-continued

Fexofenadine-containing compositions (1) produced by the procedure for Examples

| | | | | | | | | | | | | | |
|---|---|---|---|---|---|---|---|---|---|---|---|---|---|
| pH adjuster | Hydrochloric acid | | | | q.s. | q.s. | q.s. | q.s. | q.s. | q.s. | | | q.s. |
| | Citric acid hydrate | q.s. | q.s. | | | | | | | q.s. | q.s. | |
| Evaluation of solubilization | pH of formulation | 7.03 | 6.02 | 7.07 | 6.77 | 5.99 | 7.12 | 6.01 | 7.11 | 6.05 | 7.13 | 6.03 |
| | Just after production | ○ | ○ | ○ | ○ | ○ | ○ | ○ | ○ | ○ | ○ | ○ |
| RT | 1 week after production | ○ | ○ | ○ | ○ | ○ | ○ | ○ | ○ | ○ | ○ | ○ |
| | 2 weeks after production | ○ | ○ | ○ | ○ | ○ | — | ○ | ○ | ○ | ○ | ○ |
| | 3 weeks after production | ○ | ○ | ○ | ○ | ○ | — | ○ | ○ | ○ | ○ | ○ |
| | 4 weeks after production | ○ | ○ | ○ | ○ | ○ | — | ○ | ○ | ○ | ○ | ○ |
| 5° C. | 1 week after production | ○ | ○ | ○ | ○ | ○ | — | ○ | ○ | ○ | ○ | ○ |
| | 2 weeks after production | ○ | ○ | ○ | ○ | ○ | — | ○ | ○ | ○ | ○ | ○ |
| | 3 weeks after production | ○ | ○ | ○ | ○ | ○ | — | ○ | ○ | ○ | ○ | ○ |
| | 4 weeks after production | ○ | ○ | ○ | ○ | ○ | — | ○ | ○ | ○ | ○ | ○ |
| 5° C. | 1 week after production | ○ | ○ | ○ | ○ | ○ | — | ○ | ○ | ○ | ○ | ○ |
| | 2 weeks after production | ○ | ○ | ○ | ○ | ○ | — | ○ | ○ | ○ | ○ | ○ |
| | 3 weeks after production | ○ | ○ | — | ○ | ○ | — | ○ | ○ | ○ | ○ | ○ |
| | 4 weeks after production | ○ | ○ | — | ○ | ○ | — | ○ | — | ○ | ○ | ○ |

| | | | Production example | | | | | | | | |
|---|---|---|---|---|---|---|---|---|---|---|---|
| | | | 24 | 25 | 26 | 27 | 28 | 29 | 30 | 31 | 32 |
| Active ingredient | Fexofenadine hydrochloride | | | | | | | | 0.2% | | 0.3% |
| Protecting agent | Glycerin | | | | | | | | | | |
| | Mannitol | | | | | | | | | | |
| | Dipotassium glycynthizinate | | | | | | | | 1% | | 1% |
| | Hydroxypropyl-methyl cellulose | | | | | | | | | | |
| | Povidone K30 | | | | | | | | | | |
| | Methylcellulose 15 | | | | | | | | | | |
| | Methylcellulose 400 | | | 0.5% | | | | | | | |
| | Sodium carboxy-methylcellulose | | | | | 0.5% | | | | | |
| pH adjuster | Hydrochloric acid | | q.s. | | q.s. | | q.s. | | q.s. | | |
| | Citric acid hydrate | | | q.s. | | q.s. | | q.s. | | q.s. | q.s. |
| Evaluation of solubilization | pH of formulation | | 7.07 | 6.03 | 7.11 | 6.05 | 6.00 | 6.13 | 6.08 | 5.99 | 6.14 |
| | Just after production | | ○ | ○ | ○ | ○ | ○ | ○ | ○ | ○ | ○ |
| RT | 1 week after production | | ○ | ○ | ○ | ○ | ○ | — | — | — | — |
| | 2 weeks after production | | ○ | ○ | ○ | — | ○ | — | — | — | — |
| | 3 weeks after production | | ○ | ○ | ○ | — | ○ | — | — | — | — |
| | 4 weeks after production | | ○ | ○ | ○ | — | ○ | — | — | — | — |
| 5° C. | 1 week after production | | ○ | ○ | ○ | — | ○ | — | — | — | — |
| | 2 weeks after production | | ○ | ○ | ○ | — | ○ | — | — | — | — |
| | 3 weeks after production | | ○ | ○ | ○ | — | ○ | — | — | — | — |
| | 4 weeks after production | | ○ | ○ | ○ | — | ○ | — | — | — | — |
| 5° C. | 1 week after production | | ○ | ○ | ○ | — | ○ | ○ | ○ | ○ | ○ |
| | 2 weeks after production | | ○ | ○ | ○ | — | ○ | ○ | ○ | ○ | ○ |
| | 3 weeks after production | | ○ | ○ | ○ | — | ○ | ○ | ○ | ○ | ○ |
| | 4 weeks after production | | ○ | ○ | ○ | — | ○ | ○ | ○ | ○ | ○ |

TABLE 5

Fexofenadine-containing compositions (2) produced by the procedure for Examples

| | | \multicolumn{10}{c}{Production example} |
|---|---|---|---|---|---|---|---|---|---|---|---|
| | | 33 | 34 | 35 | 36 | 37 | 38 | 39 | 40 | 41 | 42 |
| Active ingredient | Fexofenacine hydrochloride | 0.1% | | 0.1% | | 0.1% | | 0.1% | | 0.1% | |
| Protecting agent | Propylene glycol | | 4% | | | | | | | | |
| | Macrogol (PEG400) | | | | 4% | | | | | | |
| | Macrogol (PEG4000) | | | | | | 1.5% | | | | |
| | Macrogol (PEG6000) | | | | | | | | 1.5% | | |
| | D-sorbitol | | | | | | | | | | 1% |
| | Chondroltin sulfate | | | | | | | | | | |
| | N-Acetylglucosamine | | | | | | | | | | |
| | Polysorbate 80 (TO-10M) | | | | | | | | | | |
| | Polyoxyethylene hydrogenated castor oil (HCO60) | | | | | | | | | | |
| pH adjuster | Hydrochloric acid | q.s. | | q.s. | | q.s. | | q.s. | | q.s. | |
| | Citric acid hydrate | | q.s. | | q.s. | | q.s. | | q.s. | | q.s. |
| Evaluation of solubilzation | pH of formulation | 5.86 | 5.66 | 6.06 | 5.82 | 6.10 | 6.07 | 6.07 | 6.01 | 5.71 | 5.71 |
| | Just after production | ○ | ○ | ○ | ○ | ○ | ○ | ○ | ○ | ○ | ○ |
| RT | 1 week after production | ○ | ○ | ○ | ○ | ○ | ○ | ○ | ○ | ○ | ○ |
| | 2 weeks after production | ○ | ○ | ○ | ○ | ○ | ○ | ○ | ○ | ○ | ○ |
| | 3 weeks after production | ○ | ○ | — | ○ | ○ | ○ | — | ○ | ○ | ○ |
| | 4 weeks after production | ○ | ○ | — | ○ | — | — | — | ○ | ○ | ○ |
| 5° C. | 1 week after production | ○ | ○ | — | ○ | — | — | — | ○ | ○ | ○ |
| | 2 weeks after production | ○ | ○ | — | ○ | — | — | — | ○ | ○ | ○ |
| | 3 weeks after production | ○ | ○ | — | ○ | — | — | — | ○ | ○ | ○ |
| | 4 weeks after production | ○ | ○ | — | ○ | — | — | — | — | ○ | ○ |
| 40° C. | 1 week after production | ○ | — | — | ○ | — | — | — | — | — | — |
| | 2 weeks after production | ○ | — | — | ○ | — | — | — | — | — | — |
| | 3 weeks after production | ○ | — | — | ○ | — | — | — | — | — | — |
| | 4 weeks after production | — | — | — | — | — | — | — | — | — | — |

| | | \multicolumn{8}{c}{Production example} |
|---|---|---|---|---|---|---|---|---|---|
| | | 43 | 44 | 45 | 46 | 47 | 48 | 49 | 50 |
| Active ingredient | Fexofenacine hydrochloride | 0.1% | | 0.1% | | 0.1% | | 0.1% | |
| Protecting agent | Propylene glycol | | | | | | | | |
| | Macrogol (PEG400) | | | | | | | | |
| | Macrogol (PEG4000) | | | | | | | | |
| | Macrogol (PEG6000) | | | | | | | | |
| | D-sorbitol | | 1% | | | | | | |
| | Chondroltin sulfate | | | | 1% | | | | |
| | N-Acetylglucosamine | | | | | | 0.2% | | |
| | Polysorbate 80 (TO-10M) | | | | | | | | 0.5% |
| | Polyoxyethylene hydrogenated castor oil (HCO60) | | | | | | | | |
| pH adjuster | Hydrochloric acid | q.s. | | q.s. | | q.s. | | q.s. | |
| | Citric acid hydrate | | q.s. | | q.s. | | q.s. | | q.s. |
| Evaluation of solubilzation | pH of formulation | 5.83 | 6.10 | 5.91 | 6.10 | 5.89 | 6.09 | 6.02 | 6.04 |
| | Just after production | ○ | ○ | ○ | ○ | ○ | ○ | ○ | ○ |
| RT | 1 week after production | ○ | ○ | ○ | ○ | — | — | — | — |
| | 2 weeks after production | ○ | ○ | ○ | ○ | — | — | — | — |
| | 3 weeks after production | ○ | ○ | ○ | ○ | — | — | — | — |
| | 4 weeks after production | ○ | — | ○ | ○ | — | — | — | — |

TABLE 5-continued

Fexofenadine-containing compositions (2) produced by the procedure for Examples

| | | | | | | | | | | |
|---|---|---|---|---|---|---|---|---|---|---|
| 5° C. | 1 week after production | ○ | — | ○ | ○ | — | — | — | — |
| | 2 weeks after production | ○ | — | ○ | ○ | — | — | — | — |
| | 3 weeks after production | ○ | — | ○ | ○ | — | — | — | — |
| | 4 weeks after production | ○ | — | ○ | ○ | — | — | — | — |
| 40° C. | 1 week after production | — | — | — | — | — | — | — | — |
| | 2 weeks after production | — | — | — | — | — | — | — | — |
| | 3 weeks after production | — | — | — | — | — | — | — | — |
| | 4 weeks after production | — | — | — | — | — | — | — | — |

TABLE 6

Fexofenadine-containing compositions produced by the procedure for Comparative Examples

| | | Comparative production example | | | | | | | |
|---|---|---|---|---|---|---|---|---|---|
| | | 1 | 2 | 3 | 4 | 5 | 6 | 7 | 8 |
| Active Ingredient | Fexofenadine hydrochloride | | | | 0.1% | | | | |
| Protecting agent | Glycerin | 2% | | | | | | | |
| | Propylene glycol | | 1% | | | | | | |
| | Macrogol (PEG400) | | | 0.10% | | | | | |
| | Macrogol (PEG6000) | | | | 0.10% | | | | |
| | D-sorbitol | | | | | 1% | | | |
| | Mannitol | | | | | | 0.80% | | |
| | Dipotassium glycyrrhizinate | | | | | | | 1% | |
| | Chondroitin sulfate | | | | | | | | 1% |
| pH adjuster (sodium hydroxide) | | | | | q.s. | | | | |
| Evaluation of solubilization | Just after production | x | x | x | x | x | x | x | x |

As is clear from Tables 4 and 5 above, when basification and subsequent addition of the protecting agent were performed, a micelle in which an anionic micelle was protected by the protecting agent was formed, and even after the pH was adjusted to near-neutral, the formed micelle was maintained in such a state and fexofenadine was successfully solubilized.

In contrast, as is clear from Table 6 above, Comparative Examples, in which the protecting agent was added without prior basification, failed to form an anionic micelle, failed to form a micelle in which the anionic micelle was protected by the protecting agent, and failed to solubilize fexofenadine. Test Example 2: Other ingredients having a functional group capable of being anionized under basic conditions Using rebamipide, indomethacin, L-carbocysteine, ibuprofen, and ursodeoxycholic acid instead of fexofenadine as an ingredient having a functional group capable of being anionized under basic conditions, liquid compositions containing these ingredients were produced based on the compositional ratios shown in Table 7 in the same manner as in Test Example 1. Solubilization of the ingredient in each sample was evaluated in the same manner as in Test Example 1, just after production and 1 week after production (conditions:uncontrolled room temperature, 40° C.) (Table 7). In Table 7, the circle symbol indicates that no precipitation was visually observed.

TABLE 7

Sparingly soluble substance-containing compositions produced by the procedure for Examples

| | | Production example | | | | | | | | | | | | | |
|---|---|---|---|---|---|---|---|---|---|---|---|---|---|---|
| | | 51 | 52 | 53 | 54 | 55 | 56 | 57 | 58 | 59 | 60 | 61 | 62 | 63 | 64 |
| Active ingredient | Rebamipide | 2% | 2% | | | | | | | | | | | | |
| | Indomethacin | | | 0.25% | 0.25% | 0.25% | 0.25% | | | | | | | | |
| | L-carbocysteine | | | | | | | 3% | 3% | 3% | 3% | | | | |
| | Ibuprofen | | | | | | | | | | | 1% | 1% | | |
| | Ursodeoxycholic acid | | | | | | | | | | | | | 0.15% | 0.15% |

TABLE 7-continued

Sparingly soluble substance-containing compositions produced by the procedure for Examples

| | | Production example | | | | | | | | | | | | | |
|---|---|---|---|---|---|---|---|---|---|---|---|---|---|---|
| | | 51 | 52 | 53 | 54 | 55 | 56 | 57 | 58 | 59 | 60 | 61 | 62 | 63 | 64 |
| Protecting agent | Glycerin | 2% | 2% | 2% | 2% | 2% | 2% | 2% | 2% | 2% | 2% | 2% | 2% | 2% | 2% |
| | Hydroxypropyl-methyl cellulose | | 0.3% | 0.3% | 0.3% | 0.3% | 0.3% | 0.3% | 0.3% | 0.3% | 0.3% | 0.3% | 0.3% | 0.3% | 0.3% |
| | Povidone K30 | 2% | 2% | | | | | | | | | | | | |
| pH adjuster | Hydrochloric acid | q s. | | q.s. | q.s. | | | q.s. | q.s. | | | q.s. | | q s. | |
| | Citric acid hydrate | | q.s. | | | q.s. | q.s. | | | q.s. | q.s. | | q.s. | | q.s. |
| Evaluation of solublization | pH of formulation | 7.21 | 7.15 | 6.05 | 7.03 | 6.06 | 7.04 | 6.20 | 7.22 | 6.21 | 7.24 | 7.24 | 7.24 | 7.22 | 7.25 |
| | Just after production | ○ | ○ | ○ | ○ | ○ | ○ | ○ | ○ | ○ | ○ | ○ | ○ | ○ | ○ |
| | RT, 1 week after production | ○ | ○ | ○ | ○ | ○ | ○ | ○ | ○ | ○ | ○ | ○ | ○ | ○ | ○ |
| | 40° C. 1 week after production | ○ | ○ | ○ | ○ | ○ | ○ | ○ | ○ | ○ | ○ | ○ | ○ | ○ | ○ |

As is clear from Table 7 above, similar results were obtained for the above ingredients as with fexofenadine. More specifically, when basification and subsequent addition of the protecting agent were performed, a micelle in which an anionic micelle was protected by the protecting agent was formed, and even after the pH was adjusted to near-neutral, the formed micelle was maintained in such a state and every test ingredient was successfully solubilized.

(2) Ingredient Having a Functional Group Capable of Being Cationized Under Acidic Conditions Test Example 3: Brinzolamide Brinzolamide-containing liquid compositions were produced by the procedure shown in Table 8 below. Solubilization of brinzolamide in each liquid composition was evaluated just after production and 1 to 4 weeks after production (conditions:uncontrolled room temperature, 5° C. or 40° C.) (Tables 9 and 10). In Tables 9 and 10, the circle symbol indicates that, no precipitation was visually observed, the cross symbol indicates that precipitation was visually observed, and "-" indicates "not tested". In the case where precipitation was observed under certain conditions, the examination under the same conditions was discontinued.

TABLE 8

| Examples | Comparative Examples |
|---|---|
| 1) Prepare 4 mL of purified water. | 1) Prepare 4 mL of purified water. |
| 2) Add brinzolamide at a final concentration of 0.2% (w/v) (see Table 9). | 2) Add brinzotamide at a final concentration of 0.2% (w/v) (see Table 10). |
| 3) Adjust the pH to 2 with dilute hydrochloric acid. | 3) (This step is not performed in Comparative Example.) |
| 4) Add an ethanol solution containing a protecting agent (tyloxapol, or in the case of reference examples, glycerin and hypromellose) (see Table 9). | 4) Add a protecting agent (tyloxapol) (see Table 10). |
| 5) Add a surfactant (see Table 9). | 5) Add a surfactant (see Table 10). |
| 6) Add water to a final volume of 5 mL. | 6) Add water to a final volume of 5 mL. |
| 7) Adjust the pH to near-neutral with 2.0N sodium hydroxide (see Table 9). | 7) Adjust the pH to nearneutral with 2.0N dilute hydrochloric acid. |

TABLE 9

Brinzolamide-containing compositions (1) produced by the procedure for Examples

| | | Production example | | | | | | | |
|---|---|---|---|---|---|---|---|---|---|
| | | (Reference Example 1) | 65 | (Reference Example 2) | 67 | 68 | 69 | 70 | 71 | 72 |
| Active Ingredient | Brinzolamide | | | | 0.2% | | | | | |
| Protecting agent | Glycerin | 2% | | 2% | | | | | | |
| | Hydroxypropylmethyl cellulose | 0.3% | | 0.3% | | | | | | |
| | Tyloxapol | | 0.1% | | 0.1% | 0.1% | 0.1% | 0.1% | 0.1% | 0.1% |

TABLE 9-continued

Brinzolamide-containing compositions (1) produced by the procedure for Examples

| | | Production example | | | | | | | | |
|---|---|---|---|---|---|---|---|---|---|---|
| | | (Reference Example 1) | 65 | (Reference Example 2) | 67 | 68 | 69 | 70 | 71 | 72 |
| Surfactant | Polysorbate 80 (TO-10M) | | | | | 0.2% | | | | |
| | Polyoxyethylene hydrogenated castor oil (HCO60) | | | | | | 0.5% | | | |
| | Polyethylene glycol monostearate (MYS-40) | | | | | | | 0.1% | | |
| | Macrogol (PEG400) | | | | | | | | | 1.5% | |
| | Macrogol (PEG4000) | | | | | | | | | | 1.5% |
| pH adjuster | Sodium hydroxide | q.s. | q.s. | q.s. | q.s. | q.s. | q.s. | q.s. | q.s. | q.s. |
| Evaluation of solubilization | pH of formulation | 7.00 | 7.00 | 6.00 | 6.00 | 6.00 | 6.00 | 6.00 | 6.00 | 6.00 |
| | Just after production | ? | ? | ? | ? | ? | ? | ? | ? | ? |
| RT | 1 week after production | x | ? | x | ? | ? | ? | ? | ? | ? |
| | 2 weeks after production | — | x | — | x | ? | ? | ? | ? | ? |
| | 3 weeks after production | — | — | — | — | ? | ? | ? | ? | ? |
| | 4 weeks after production | — | — | — | — | ? | ? | ? | ? | ? |
| 40° C. | 1 week after production | — | — | — | — | ? | ? | ? | ? | ? |

TABLE 10

Brinzolamide-containing compositions produced by the procedure for Comparative Examples

| | | Comparative production example | | | | | |
|---|---|---|---|---|---|---|---|
| | | 9 | 10 | 11 | 12 | 13 | 14 |
| Active Ingredient | Brinzolamide | | | 0.2% | | | |
| Protecting agent | Tyloxapol | 0.1% | | | | | |
| Surfactant | Polysorbate 80 (TO-10M) | | 0.2% | | | | |
| | Polyoxyethylene hydrogenated castor oill (HCO60) | | | 0.5% | | | |
| | Polyethylene glycol monostearate (MYS-40) | | | | 0.1% | | |
| | Macrogol (PEG400) | | | | | 1.5% | |
| | Macrogol (PEG6000) | | | | | | 1.5% |
| pH adjuster (dilute hydrochloric acid) | | | | q.s. | | | |
| Evaluation of solubilization | Just after production | x | x | x | x | x | x |

As is clear from Table 9 above, when acidification and subsequent addition of the protecting agent were performed, a micelle in which a cationic micelle was protected by the protecting agent was formed, and even after the pH was adjusted to near-neutral, the formed micelle was maintained in such a state and brinzolamide was successfully solubilized.

In contrast, as is clear from Table 10 above. Comparative Examples, in which the protecting agent was added without prior acidification, failed to form a cationic micelle, failed to form a micelle in which the cationic micelle was protected by the protecting agent, and failed to solubilize brinzolamide.

Test Example 4: Other Ingredients Having a Functional Group Capable of Being Cationized Under Acidic Conditions Using trimebutine, ethyl aminobenzoate, baclofen, metoclopramide, and lidocaine hydrochloride instead of brinzolamide as an ingredient having a functional group capable of being cationized under acidic conditions, liquid compositions containing these ingredients were produced based on the compositional ratios shown in Table 11 in the same manner as in Test Example 3. Solubilization of the ingredient in each sample was evaluated in the same manner as in Test Example 3, just after production and 1 week, after production (conditions:uncontrolled room temperature, 40° C.) (Table 11). In Table 11, the circle symbol indicates that no precipitation was visually observed.

TABLE 11

Sparingly soluble substance-containing compositions produced by the procedure for Examples

| | | Production example | | | | | | |
|---|---|---|---|---|---|---|---|---|
| | | 73 | 74 | 75 | 76 | 77 | 78 | 79 |
| Active Ingredient | Trimebutine | 0.05% | | | | | | |
| | Ethyl aminobenzoate | | 0.2% | | | | | |
| | Baclofen | | | 0.2% | | | | |
| | Metoclopramide | | | | | 1% | | |
| | Lidocaine hydrochloride | | | | | | | 0.4% |
| Protecting agent | Tyloxapol | | | | 0.1% | | | |
| Surfactant | Macrogol (PEG4000) | | | | 1.5% | | | |
| pH adjuster | Sodium hydroxide | | | | q.s. | | | |
| Evaluation of solubilization | pH of formulation | 5.90 | 6.00 | 5.80 | 6.80 | 5.80 | 6.80 | 7.20 |
| | Just after production | ? | ? | ? | ? | ? | ? | ? |
| | RT, 1 week after production | ? | ? | ? | ? | ? | ? | ? |
| | 40° C., 1 week after production | ? | ? | ? | ? | ? | ? | ? |

As is clear from Table 11 above, similar results were obtained for the above ingredients as with brinzolamide. More specifically, when acidification and subsequent addition of the protecting agent were performed, a micelle in which a cationic micelle was protected by the protecting agent was formed, and even after the pH was adjusted to near-neutral, the formed micelle was maintained in such a state and every test ingredient was successfully solubilized.

(3) Confirmation of Micelle Formation (3-1) Confirmation 1

<1> For preparation of the samples shown in Table 12 below, the indicated amounts of fexofenadine hydrochloride were weighed out in beakers, and exact 5 mL of an aqueous sodium hydroxide solution adjusted to pH 12.5 was added to each beaker, followed by 15-minute stirring for dissolution. In the preparation of samples 3 to 7, the amounts of solid sodium hydroxide described in Table 12 were added for complete dissolution.

<2> All the fexofenadine aqueous solutions prepared in the above <1> were adjusted to pH 12.5.

<3> Ultraviolet absorption spectrum of each sample was measured, and the absorbance was read at the wavelength of 268 nm (Table 12).

Figure 9:
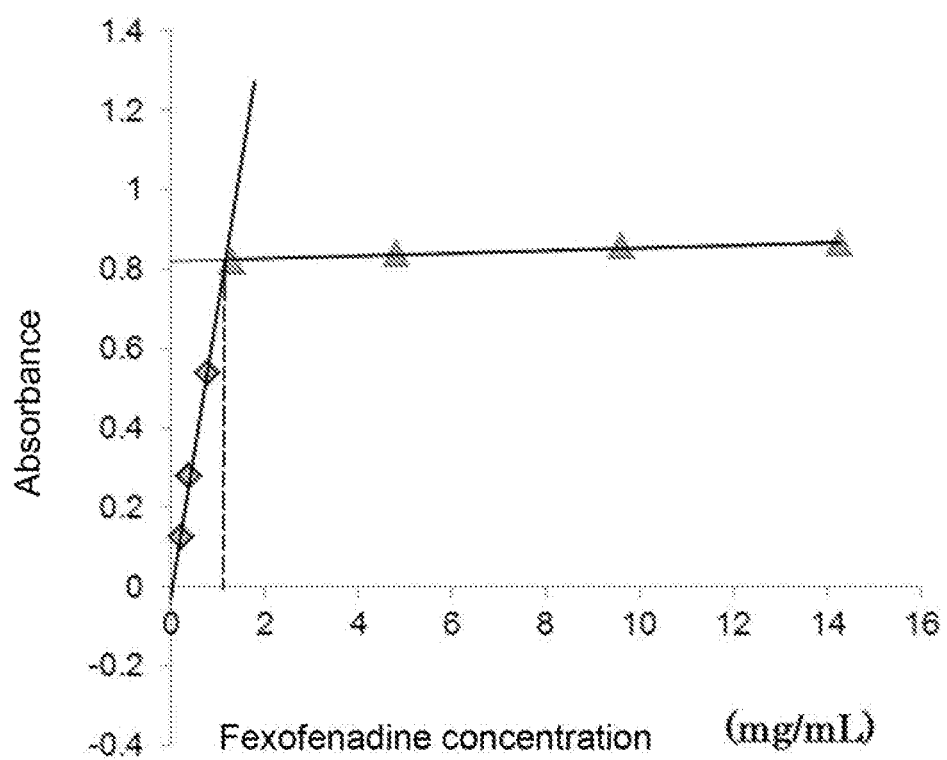
FIG. 9 shows the absorbances of samples 1 to 7 measured at a wavelength of 268 nm.

The absorbances of all the samples are shown in Table 12. FIG. 9 show a graph plotting the absorbance on the vertical axis and the fexofenadine concentration on the horizontal axis.

TABLE 12

| | Amount of fexofenadine weighed (mg) | Amount of NaOH (aq) used in Step <2> | Fexofenadine concentration (mg/mL) | Absorbance (268 nm) |
|---|---|---|---|---|
| Sample 1 | 1 | 0 | 0.2 | 0.125 |
| Sample 2 | 2 | 0 | 0.38 | 0.279 |
| Sample 3 | 4 | 0.25 | 0.76 | 0.525 |
| Sample 4 | 7 | 0.45 | 1.28 | 0.823 |
| Sample 5 | 25 | 0.2 | 4.81 | 0.865 |
| Sample 6 | 50 | 0.2 | 9.62 | 0.883 |
| Sample 7 | 75 | 0.25 | 14.3 | 0.892 |

In FIG. 9, a straight line was drawn by connecting the points at low fexofenadine concentrations. Another straight line was drawn by connecting the points at high fexofenadine concentrations.

The intersection of the two straight lines represents critical micelle concentration (CMC), which was 1 mg/mL (0.1% w/v).

These results confirmed that a 0.1% w/v fexofenadine anionic solution has a micellar structure.

(3-2) Confirmation 2

Ultraviolet absorption spectra of samples 1 to 7 were measured at around the respective maximal absorption wavelengths ($\lambda$max) (see Table 13 below).

TABLE 13

| | Fexofenadine concentration (mg/mL) | $\lambda$max (nm) |
|---|---|---|
| Sample 1 | 0.20 | 266.8 |
| Sample 2 | 0.38 | 267 |
| Sample 3 | 0.76 | 267.9 |
| Sample 4 | 1.28 | 268.8 |
| Sample 5 | 4.81 | 271.4 |
| Sample 6 | 9.62 | 272.7 |
| Sample 7 | 14.3 | 273.6 |

Figure 10:
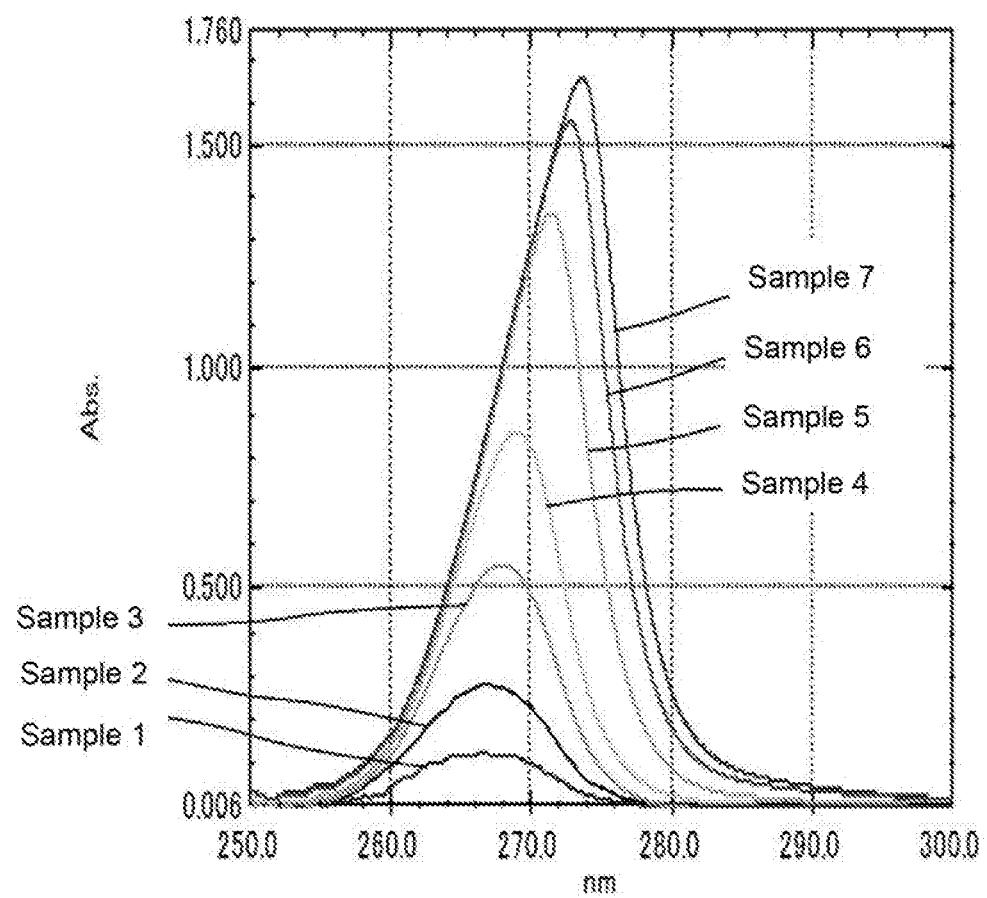
FIG. 10 shows the ultraviolet absorption spectra of samples 1 to 7 measured around at the respective maximal absorption wavelengths (λmax).

The results are shown in FIG. 10. As shown in FIG. 10, in samples 4 to 7, each of which had a fexofenadine concentration higher than CMC, the spectral peak was shifted toward a longer wavelength along with a greater sample number and the peak shift between samples 4 and 7 was about 7 nm. After measurement, sample 4 was diluted to the same concentration as that of sample 2 and instantly subjected to measurement. The obtained spectrum was completely consistent with that of sample 2, showing the reversibility of the spectral shift.

These results confirmed that fexofenadine anions show J-aggregation behavior at concentrations higher than CMC, namely, in a concentration range in which micelles form.

(3-3) Confirmation 3

The anionic micelles of Production Example 80 shown in Table 14 below were produced. In addition, the micelles of Production Examples 81 and 82 were produced according to the procedure for Examples described in Table 3 above.

TABLE 14

| Production Example | Fexotenadine | HPMC (TC-5E) | Glycerin | Hydrochloric acid | pH |
|---|---|---|---|---|---|
| 80 | 0.1% (w/v) | — | — | — | 12.5 |
| 81 | 0.1% (w/v) | 0.1% | 0.1% | q.s. | 7.02 |
| 82 | 0.1% (w/v) | 0.1% | — | q.s. | 7.04 |

The particle size distribution of the anionic micelles of Production Example 80 and the micelles of Production Examples 81 and 82 was measured with a dynamic light scattering (DLS) type nanopowder particle size distribution measuring instrument, (manufactured by Spectris, Malvern Panalytical, Zetasizer nano ZS).

Figure 11:
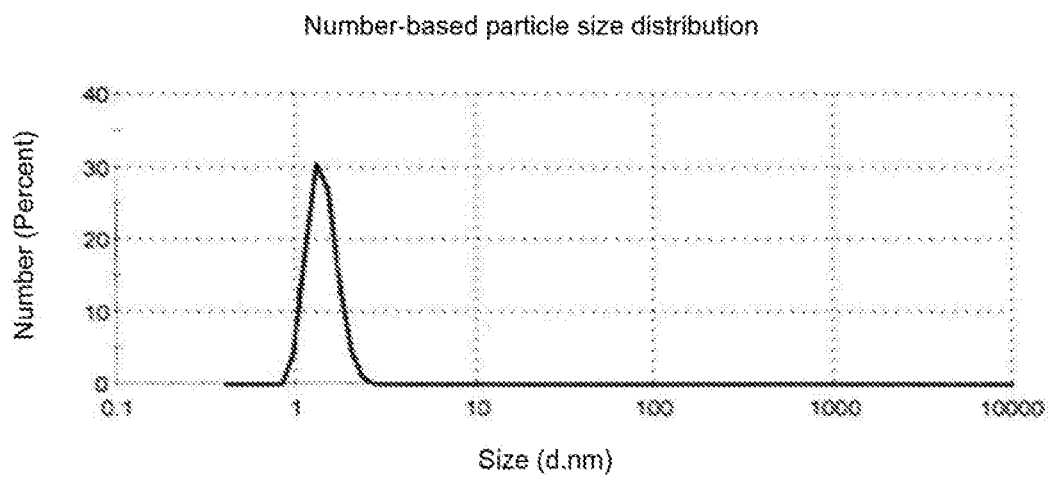
FIG. 11 shows the measured particle size distribution of the anionic micelles of Production Example 80.
Figure 12:
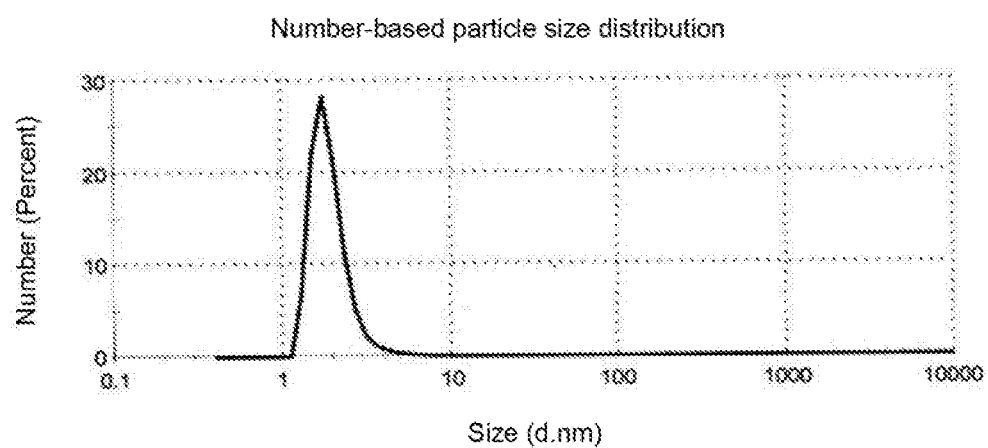
FIG. 12 shows the measured particle size distribution of the micelles of Production Example 81.
Figure 13:
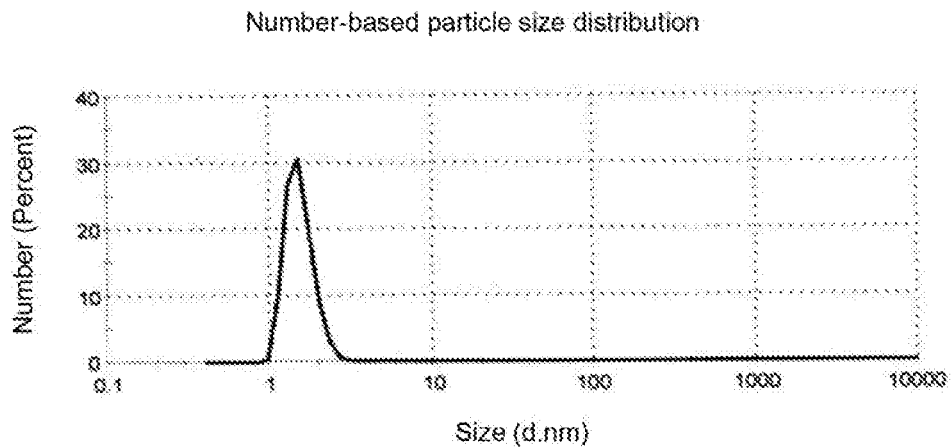
FIG. 13 shows the measured particle size distribution of the micelles of Production Example 82.

The results showed that the diameter of the anionic micelles of Production Example 80 was about 1.4 nm (Table 15, FIG. 11), the diameter of the micelles of Production Example 81 was about 1.9 nm (Table 16, FIG. 12), and the diameter of the micelles of Production Example 82 was about 1.5 nm (Table 17, FIG. 13).

The conditions for measuring the particle size distribution of the anionic micelles of Production Example 80 and the micelles of Production Examples 81 and 82 were as follows.
Production Example 80:
Conditions: sample RI: 1.60° dispersion medium RI: 1.474, viscosity: 0.94 mpa·s temperature: 25° C.
Production Example 81:
Conditions: sample RI: 1.60° dispersion medium RI: 1.337, viscosity: 1.24 mpa·s temperature: 25° C.
Production Example 82:
Conditions: sample RI: 1.60° dispersion medium RI: 1.337, viscosity: 1.15 mpa·s temperature: 25° C.

TABLE 15

| Diameter (nm) | % of total number | Width (nm) |
|---|---|---|
| 1.410 | 100.0 | 0.2690 |
| 0.000 | 0.0 | 0.000 |
| 0.000 | 0.0 | 0.000 |

TABLE 16

| Diameter (nm) | % of total number | Width (nm) |
|---|---|---|
| 1.936 | 100.0 | 0.6204 |
| 0.000 | 0.0 | 0.000 |
| 0.000 | 0.0 | 0.000 |

TABLE 17

| Diameter (nm) | % of total number | Width (nm) |
|---|---|---|
| 1.535 | 9.6 | 0.3116 |
| 5.075 | 0.4 | 0.000 |
| 0.000 | 0.0 | 0.000 |

The above particle diameter comparison showed that fexofenadine in the micelle of Production Example 81 was covered by hydroxypropyl methylcellulose (herein also called hypromellose or HPMC), which was further covered by glycerin.

(3-4) Confirmation 4

To 5 mL of the anionic micelle-containing solution of Production Example 80, 5 mL of the micelle-containing solution of Production Example 81 just after production or after 6-month storage at 40° C., or 5 mL of the micelle-containing solution of Production Example 80 just after production or after 6-month storage at 40° C., 100 mg of sodium chloride was added. Instantly, fexofenadine was precipitated in all the solutions. These results were due to micelle disintegration and confirmed that micelles had been formed in all the solutions.

(4) Confirmation as to the Formulation Described in Example 5 in JP-W 2003-519083

The following test was performed to confirm that the formulation described in Example 5 in JP-W 2003-519083 was different from the micelle β in the present invention.
(4-1)
The formulation of Example 5 in JP-W 2003-519083 was prepared as described in the literature and left stand at uncontrolled room temperature. The results are shown in Table 18 below.

TABLE 18

| 1 hour after preparation | 2 hours after preparation | 3 hours after preparation |
|---|---|---|
| No precipitation | Slight precipitation | Massive precipitation |

(4-2)
The formulation of Example 5 in JP-W 2003-519083 was prepared as described in the literature, and the pH of the formulation was measured. The pH of the formulation was 3.16.

When a 1.0 N aqueous sodium hydroxide solution was added to the formulation, white turbidity appeared at pH 6, and massive precipitation was observed at pH 7.

To summarize the above, the formulation described in Example 5 in JP-W 2003-519083 was significantly unstable at room temperature and was only capable of solubilizing fexofenadine at a very low pH for just 1 hour. Therefore, the solubilization method of JP-W 2003-519083 is not practical, in particular for pharmaceutical use.

(5) Drug Efficacy Test of Fexofenadine

Rats (Wistar strain, male, 5 weeks old at delivery, purchased from Japan SLC, Inc) were passively sensitized by injection of pre-prepared anti-ovalbumin antiserum (antibody titer 3) into the lower palpebral conjunctivae of both eyes under anesthesia (10 μL/eye, n×6 per group). After 48 hours, 1 mL of a challenge solution was intravenously administered to induce local allergic reaction in the conjunctiva. A test solution was ocularly administered 15 minutes before and just before allergy induction (2 times in total). Thirty minutes after the challenge, each rat was euthanized, and the palpebral conjunctiva was excised along with the conjunctival fornix. The weight of the tissue was measured, and an extraction solvent was added to the tissue, followed by overnight extraction. After that, the extract solution was centrifuged, and the absorbance of the supernatant was measured at 620 nm. The rats in group 3 were given Production Example 14, and the rats in group 4 were given Production Example 32.
Evaluation Method Allergic reaction causes vascular hyperpermeability, resulting in Evans blue leakage. A smaller amount of dye leakage means that vascular hyperpermeability is more suppressed, indicating that the test solution has antiallergic effect. The amount of dye leakage per unit tissue weight (μg/g) was determined using a standard curve prepared beforehand and regarded as a measure of suppressive effect.
 Group 1: Physiological saline
 Group 2: Zaditen (registered trademark) eye drop 0.05%
 Group 3: Fexofenadine-solubilized formulation 0.1%
 Group 4: Fexofenadine-solubilized formulation 0.3%

The results are shown in FIG. 14. As is clear from FIG. 14, formation of a micelle in which an anionic micelle formed from fexofenadine as a structural unit was protected by the protecting agent was effective for maintaining the drug effect of fexofenadine and preventing it from deteriorating.

INDUSTRIAL APPLICABILITY

The present invention provides a solubilization technology for sparingly water-soluble ingredients and can be applied to all technical fields, in particular to the pharmaceutical field.

The invention claimed is:

1. A micelle comprising an anionic micelle and a protecting agent surrounding the anionic micelle, the anionic micelle being formed from, as a structural unit, an ingredient that has a functional group capable of being anionized under basic conditions and has anionic micelle-forming ability, the protecting agent protecting the anionic micelle, and wherein the protecting agent has a hydroxy group (—OH) in water.

2. The micelle according to claim 1, wherein the protecting agent has an atom bound to an anionized functional group of the anionic micelle, and the electron density of the atom is smaller than the electron density of the anionized functional group of the anionic micelle.

3. The micelle according to claim 1, wherein the atom in the protecting agent is bound to the anionized functional group of the anionic micelle via a hydrogen bond.

4. The micelle according to claim 1, wherein the protecting agent is at least one selected from the group consisting of polyethylene glycol, glycerin, propylene glycol, sorbitol, mannitol, N-acetylglucosamine, chondroitin sulfate, glycyrrhizinic acid, hydroxypropylmethyl cellulose, methylcellulose, carboxymethyl cellulose, polyoxyethylene hydrogenated castor oil, and polysorbate 80.

5. The micelle according to claim 1, wherein the ingredient has a low water solubility in a neutral pH range of 6 to 8.

6. The micelle according to claim 1, wherein the ingredient is at least one selected from the group consisting of fexofenadine, rebamipide, indomethacin, L-carbocysteine, ibuprofen, and ursodeoxycholic acid, or a salt thereof.

7. A solution comprising the micelle according to claim 1, the solution comprising a solubilized ingredient having a functional group capable of being anionized under basic conditions.

8. The solution according to claim 7, wherein the ingredient is present at a concentration of 0.01 to 5.0% (w/v).

9. The solution according to claim 7, wherein the solution has a pH of 5 to 9 during long-term storage.

10. The solution according to claim 7, wherein the solution is an eye drop or a nasal drop.

11. A method of producing a micelle, the micelle comprising an anionic micelle and a protecting agent, the anionic micelle being formed from, as a structural unit, an ingredient that has a functional group capable of being anionized under basic conditions and has anionic micelle-forming ability, the protecting agent protecting the anionic micelle, and wherein the protecting agent has a hydroxy group (—OH) in water, the method comprising the following steps (A) and (B):
(A) suspending, in water, the ingredient that has a functional group capable of being anionized under basic conditions and has anionic micelle-forming ability, and subsequently basifying the resulting suspension; and
(B) adding the protecting agent.

12. A micelle produced by the production method according to claim 11, the micelle comprising an anionic micelle and a protecting agent, the anionic micelle being formed from, as a structural unit, an ingredient that has a functional group capable of being anionized under basic conditions and has anionic micelle-forming ability, the protecting agent protecting the anionic micelle, and wherein the protecting agent has a hydroxy group (—OH) in water.

13. A method for increasing the solubility of an ingredient that has a functional group capable of being anionized under basic conditions and has anionic micelle-forming ability, the method comprising:
a step of forming an anionic micelle from the ingredient that has a functional group capable of being anionized under basic conditions and has anionic micelle-forming ability, and
a step of protecting the anionic micelle with a protecting agent, wherein the protecting agent has a hydroxy group (—OH) in water.

* * * * *